(12) United States Patent
Kim et al.

(10) Patent No.: US 10,533,987 B2
(45) Date of Patent: Jan. 14, 2020

(54) POROUS SEMICONDUCTOR METAL OXIDE COMPLEX NANOFIBERS INCLUDING NANOPARTICLE CATALYST FUNCTIONALIZED BY NANO-CATALYST INCLUDED WITHIN METAL-ORGANIC FRAMEWORK, GAS SENSOR AND MEMBER USING THE SAME, AND METHOD OF MANUFACTURING THE SAME

(71) Applicant: KOREA ADVANCED INSTITUTE OF SCIENCE AND TECHNOLOGY, Daejeon (KR)

(72) Inventors: Il-Doo Kim, Daejeon (KR); Wontae Koo, Daejeon (KR); Jisu Jang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 451 days.

(21) Appl. No.: 15/191,986

(22) Filed: Jun. 24, 2016

(65) Prior Publication Data
US 2017/0003272 A1    Jan. 5, 2017

(30) Foreign Application Priority Data
Jul. 2, 2015    (KR) .......................... 10-2015-0094550

(51) Int. Cl.
*G01N 33/497*    (2006.01)
*B01J 23/60*    (2006.01)

(52) U.S. Cl.
CPC ............ *G01N 33/497* (2013.01); *B01J 23/60* (2013.01); *G01N 2033/4975* (2013.01)

(58) Field of Classification Search
CPC .................................................. G01N 33/497; G01N 2033/4975; B01J 23/60
See application file for complete search history.

(56) References Cited

U.S. PATENT DOCUMENTS

2016/0226076 A1*    8/2016   Huang ................... H01M 4/925

OTHER PUBLICATIONS

Wang, Weixia, et al. "Metal-organic framework as a host for synthesis of nanoscale Co3O4 as an active catalyst for Co oxidation." Catalysis Communications 12.10 (2011): 875-879.*
Bala, Sukhen, et al. "Co—MOF as a sacrificial template: manifesting a new Co 3 O 4/TiO 2 system with ap-n heterojunction for photocatalytic hydrogen evolution." Journal of Materials Chemistry A 3.40 (2015): 20288-20296.*

(Continued)

*Primary Examiner* — Robert J Eom
(74) *Attorney, Agent, or Firm* — Ferguson Case Orr Paterson

(57) ABSTRACT

The inventive concepts relate to a member for a gas sensor, a gas sensor using the same, and a method of manufacturing the same. More particularly, the inventive concepts relate to a gas sensor member using a porous semiconductor metal oxide complex nanofiber functionalized by uniformly distributing porous first metal oxide particles, including metal nanoparticle catalysts synthesized using a metal-organic framework, in the inside and on a surface of a second metal oxide nanofiber, a gas sensor using the same, and a method of manufacturing the same.

20 Claims, 13 Drawing Sheets

(56) References Cited

OTHER PUBLICATIONS

Jiang, Hai-Long, et al. "Au@ ZIF-8: Co oxidation over gold nanoparticles deposited to metal- organic framework." Journal of the American Chemical Society 131.32 (2009): 11302-11303.*

Miller, Derek R., Sheikh A. Akbar, and Patricia A. Morris. "Nanoscale metal oxide-based heterojunctions for gas sensing: a review." Sensors and Actuators B: Chemical 204 (2014): 250-272.*

Hwang, Sun Hye, Chanhoi Kim, and Jyongsik Jang. "SnO2 nanoparticle embedded TiO2 nanofibers—Highly efficient photocatalyst for the degradation of rhodamine B." Catalysis communications 12.11 (2011): 1037-1041.*

Fabrication of Pd Doped WO3 Nanofiber as Hydrogen Sensor; Alireza Nikfarjam,et al; ISSN 2-73-4360; p. 5, 44-55; www.mdpi.com/journal/polymers; Jan. 10, 2013.

Sensors and Actuators B: Chemical, Gas sensors using hierarchical and hollow oxide nanostructures; Jong-Heun Lee; p. 320-336; May 3, 2009.

Metal-Orcanic Framework Nanofibers via Electrospinning; Rainer Ostermann, et al; The Royal Society of Chemistry; Jun. 30, 2010; p. 442-444.

* cited by examiner

POROUS SEMICONDUCTOR METAL OXIDE COMPLEX NANOFIBERS INCLUDING NANOPARTICLE CATALYST FUNCTIONALIZED BY NANO-CATALYST INCLUDED WITHIN METAL-ORGANIC FRAMEWORK, GAS SENSOR AND MEMBER USING THE SAME, AND METHOD OF MANUFACTURING THE SAME

CROSS-REFERENCE TO RELATED APPLICATION

This U.S. non-provisional patent application claims priority under 35 U.S.C. § 119 to Korean Patent Application No. 10-2015-0094550, filed on Jul. 2, 2015, in the Korean Intellectual Property Office, the disclosure of which is hereby incorporated by reference in its entirety.

BACKGROUND

Embodiments of the inventive concepts relate to a member for a gas sensor, a gas sensor using the same, and a method of manufacturing the same. More particularly, embodiments of the inventive concepts relate to a porous semiconductor metal oxide complex nanofiber functionalized by uniformly distributing porous first metal oxide particles, including metal nanoparticle catalysts synthesized using a hollow metal-organic framework formed by combining metal ions with organic ligands, in the inside and on a surface of a second metal oxide nanofiber, a member using the same, a gas sensor using the same, and a method of manufacturing the same.

As awareness to health increases, a semiconductor metal oxide based gas sensor is being actively developed as a sensor technique capable of rapidly detecting various harmful environmental gases and of early providing harmful information or a sensor technique having high sensitivity and high selectivity to early monitor a health symptom of a human body. In particular, researches are being actively conducted for a technique capable of increasing sensitivity and selectivity with respect to a specific gas by combining a catalyst with a sensing material based on the semiconductor metal oxide. A semiconductor metal oxide based gas sensor senses a gas by using an electrical resistance variation of the semiconductor metal oxide which occurs by surface reaction occurring when a specific gas is adsorbed on and detached from a surface of the semiconductor metal oxide material. Since the semiconductor metal oxide based gas sensor analyzes a ratio of a resistance in the specific gas to a resistance in air to quantitatively sense the specific gas, a sensor system may have a simple structure and a small size and may easily work together with another device. Thus, researches are being actively conducted for a technique capable of applying the semiconductor metal oxide based gas sensor to a mobile or wearable device. In addition, the semiconductor metal oxide based gas sensor is applied in various fields such as a harmful environmental gas alarm, an alcohol drinking detector, an atmospheric pollution detector, and a sensor for sensing a terror gas. In particular, a healthcare exhalation sensor capable of early diagnosing a specific disease by sensing a biomarker gas is spotlighted. Various biomarker gases (e.g., acetone, ammonia, nitrogen monoxide, sulfureted hydrogen, toluene, and pentane) exist within a breath exhaled out from a mouth through the lungs of a human body. These gases are reported as biomarker gases for diabetes, a kidney disease, asthma, foul breath, a cancer of the lungs, and a disease of the heart.

Since the breath exhaled through the lungs of the human body includes hundreds of various gases mixed with each other, a specific biomarker gas should be selectively sensed. In addition, a biomarker gas included in the exhaled breath of the human body has a very low concentration ranging from 10 parts per billion (ppb) to 10 parts per million (ppm), and thus a gas sensor capable of accurately sensing a gas having a concentration of about 10 ppb should be developed to sense the biomarker gas. Moreover, the size of the gas sensor should be reduced to use the sensor as a real-time sensing device, and a response time and a recovery time of the gas sensor should be shorter than several seconds. The response time of the gas sensor is a time for which the gas sensor responds to the specific gas, and the recovery time of the gas sensor is a time for which the gas sensor recovers to an initial state in air. However, since the semiconductor metal oxide based gas sensor uses the principle which detects the electrical resistance variation according to the surface reaction occurring when the specific gas is adsorbed on and detached from the surface, the selectivity of the gas sensor reacting with the specific gas is reduced and the gas sensor is difficult to measure the gas having a very low concentration of several ppb. Thus, a sensing material for a gas sensor, which has high sensitivity and high selectivity, should be developed to use the semiconductor metal oxide based gas sensor as the healthcare exhalation sensor.

To allow the semiconductor metal oxide based gas sensor to have the high sensitivity and the high selectivity, various researches are being actively conducted for application and synthesis of various nanostructure based sensing materials including a nanoparticle, a nanofiber, a nanotube, a nanocube, and a hollow nanostructure. The nanostructure based sensing material has a high surface area reacting with gases, which is larger than that of a thick film. Thus, the semiconductor metal oxide based gas sensor has higher sensitivity by using the nanostructure when the semiconductor metal oxide based gas sensor uses the surface reaction between the semiconductor metal oxide material and gas molecules. In addition, when the sensing member has the hollow or porous structure, gases are easily diffused into the sensing material. Thus, the sensing material may have higher sensitivity and a higher reaction rate. In particular, a surface area of a porous nanofiber having a one-dimensional structure is six times or more greater than that of a thin layer structure, and gases are easily diffused into the porous nanofiber. Thus, the sensing member may have higher sensitivity and a higher reaction rate. In addition, when a catalyst is coupled or bonded to the porous nanofiber, the catalyst can be coupled or bonded to both an inner surface and an outer surface of the porous nanofiber shell. In other words, the porous nanofiber has a large surface area at which the catalyst reacts with a gas, and thus the sensing member including the porous nano fiber may have a higher catalyst reaction characteristic. Researches are being actively conducted for development of sensing materials having high sensitivity and selectivity by coupling various nanoparticle catalysts to the semiconductor metal oxide based sensing materials. These methods using the nanoparticle catalysts may include a chemical sensitization method and an electronic sensitization method on the basis of a principle. The chemical sensitization method may increase a concentration of gases used in the surface reaction by using a metal catalyst such as platinum (Pt) or gold (Au), thereby improving characteristics of the gas sensor. The electronic sensitization method may improve sensitivity of the gas sensor by using a variation of an oxidation number occurring by forming a metal (e.g., palladium (Pd), nickel (Ni), cobalt (Co), or silver (Ag)) into a metal oxide (e.g., PdO, NiO, $Co_2O_3$, or $Ag_2O$).

Even though researches are conducted for the development of the various nanostructure and the sensing materials to which various nanoparticle catalysts are coupled, a semiconductor metal oxide based sensing material having very high sensitivity rapidly and accurately detecting a very small amount of a gas is not commercialized. Thus, a sensing material capable of selectively sensing a very small amount of a gas should be developed to realize a healthcare exhalation sensor.

A chemical deposition method, a physical deposition method, and a chemical growth method have been developed as conventional methods of synthesizing a nanostructure. However, these methods may include complex processes, and thus process costs and process times of these methods may be increased. In other words, these methods may be difficult to be applied to mass production.

In addition, nanoparticle catalysts should be uniformly distributed on an entire region of a sensing material to effectively increase sensitivity and selectivity of a sensor. A nanoparticle catalyst may be synthesized by a polyol synthesis method corresponding to a representative method of synthesizing a nanoparticle catalyst. In this case, aggregation between nanoparticle catalysts may be caused when the catalysts are coupled to a metal oxide material. Thus, it is difficult to uniformly distribute the catalysts on and in the sensing material.

To overcome the disadvantage described above, it is necessary to manufacture a nanoparticle catalyst having a size of several nm and to synthesize a nanostructure on which nanoparticle catalysts are uniformly distributed. In addition, it is necessary to develop a sensing material having a wide surface area reacting with gases by using a simple and effective manufacturing method. As a result, it is necessary to develop a material-synthesizing technique and a sensor-manufacturing technique which are capable of selectively sensing very small amounts of biomarker gases included in exhaled breath of a human body by satisfying the necessities described above.

SUMMARY

Embodiments of the inventive concepts may provide a method of coupling first metal oxide particles to the inside and the outside of a second metal oxide nanofiber. A metal-organic framework is formed by combining metal ions with organic ligands, and nanoparticle catalysts are included in the metal-organic framework by using a nanomaterial having pores of about 1.2 nm. The first metal oxide particles are formed by oxidizing the metal ions of the metal-organic framework through a thermal treatment process.

In particular, after the thermal treatment process, metal nanoparticle catalysts included in the metal-organic framework are uniformly distributed without aggregation between catalyst particles on a surface and in the inside of the semiconductor metal oxide nanofiber. Thus, a chemical sensitization or electronic sensitization catalyst effect is shown at a single catalyst particle. In addition, embodiments of the inventive concepts may also provide a technique of synthesizing a porous semiconductor metal oxide complex nanofiber sensing material functionalized by porous first metal oxide particles that include a nanoparticle catalyst and are uniformly coupled to an inside and a surface of a second metal oxide nanofiber, and an application technique of a gas sensor using the same. The metal ions of the metal-organic framework are oxidized during the thermal treatment process to form the first metal oxide particles. The first metal oxide particles and the second metal oxide nanofiber may form heterojunctions to increase sensitivity.

To solve the above mentioned problems, embodiments of the inventive concepts may also provide a gas sensor member capable of detecting a very small amount of a gas by uniformly distributing very small nanoparticle catalysts having a size of 10 nm or less in the inside and on the outside of the porous metal oxide nanofiber without aggregation therebetween, a gas sensor using the same, and a method of manufacturing the same.

In an aspect of the inventive concepts, a metal-organic framework having a lot of pores or cavities may be synthesized, and nanoparticle catalysts may be encapsulated to be uniformly dispersed in the synthesized metal-organic framework. Thus, the nanoparticle catalysts may be embedded in porous first metal oxide particles, and the first metal oxide particles may be uniformly distributed in an inside and on an outside of a second metal oxide nanofiber. As a result, it is possible to manufacture a sensing material having a wide surface area and including the uniformly distributed nanoparticle catalysts. In an aspect, a method of manufacturing a member for a gas sensor may include step (a) of manufacturing a metal-organic framework by reacting metal ions with an organic material; step (b) of encapsulating nanoparticle catalysts in cavities of the metal-organic framework; step (c) of manufacturing a metal oxide precursor/polymer/metal-organic framework/nanoparticle catalyst complex nanofiber, in which the nanoparticle catalysts and the metal-organic framework are contained in a surface or an inside of a metal oxide precursor/polymer complex nanofiber, by an electrospinning method; step (d) of forming a porous semiconductor metal oxide complex nanofiber, which is functionalized by uniformly distributing porous first metal oxide particles including the nanoparticle catalysts in an inside and on a surface of a second metal oxide nanofiber, by performing a thermal treatment process to remove the polymer and the organic material of the metal-organic framework and to oxidize the metal oxide precursor and a metal of the metal-organic framework; step (e) of dispersing and pulverizing the porous metal semiconductor metal oxide complex nanofiber including the nanoparticle catalysts in ethanol to coat an electrode for measuring a gas sensor with the ethanol including the complex nanofiber; and step (f) of manufacturing a gas sensor array including a plurality of gas sensors in which a plurality of nanoparticle catalysts are coupled to an inside and an outside of the porous semiconductor metal oxide nanofibers.

In the step (a), the metal-organic framework may be a porous material formed by combining metal ions with organic ligands and may have various structures according to a kind thereof. In general, a unit metal-organic framework may have a sphere shape of which an inside is empty, i.e., a hollow structure. A cavity of the unit metal-organic framework may have a size of 0.9 nm to 30 nm and may be various according to a kind of the metal-organic framework. The unit metal-organic frameworks may be gathered to form a nano metal-organic framework molecular sieve having a size of a several tens nanometers or a bulk metal-organic framework molecular sieve having a size of several micrometers. For example, the metal-organic framework according to the inventive concepts may be ZIF-1, ZIF-2, ZIF-3, ZIF-4, ZIF-5, ZIF-6, ZIF-7, ZIF-8, ZIF-9, ZIF-10, ZIF-11, ZIF-12, ZIF-22, ZIF-65, ZIF-69, ZIF-71, ZIF-78, ZIF-90, ZIF-95, ZIF-9-67, or SIM-1. A metal salt used to form the metal-organic framework may include at least one of $Zn_4O$ $(CO_2)_6$, $Zn_3O(CO_2)_6$, $Cr_3O(CO_2)_6$, $In_3O(CO_2)_6$, $Ga_3O(CO_2)_6$, $Cu_2O(CO_2)_4$, $Zn_2O(CO_2)_4$, $Fe_2O(CO_2)_4$, $Mo_2O(CO_2)_4$, $Cr_2O(CO_2)_4$, $Co_2O(CO_2)_4$, $Ru_2O(CO_2)_4$, $Zr_6O_4(OH_4)$, $Zr_6O_4(CO_2)_{12}$, $Zr_6O_8(CO_2)_8$, $In(C_5HO_4N_2)_4$, $Na(OH)_2(SO_3)_3$, $Cu_2(CNS)_4$, $Zn(C_3H_3N_2)_4$, $Ni_4(C_3H_3N_2)_8$, $Zn_3O_3(CO_2)_3$, $Mg_3O_3(CO_2)_3$, $Co_3O_3(CO_2)_3$, $Ni_3O_3(CO_2)_3$, $Mn_3O_3(CO_2)_3$, $Fe_3O_3(CO_2)_3$, $Cu_3O_3(CO_2)_3$, $Al(OH)(CO_2)_2$, $VO(CO_2)_2$, $Zn(NO_3)_2$, $Zn(O_2CCH_3)$, $Co(NO_3)_2$, or $Co(O_2CCH_3)$. The organic ligands used to form the metal-organic framework may include at least one of oxalic acid, fumaric acid, $H_2BDC$, $H_2BDC$—Br, $H_2BDC$—OH, $H_2BDC$—$NO_2$, $H_2BDC$—$NH_2$, $H_4DOT$, $H_2BDC$-$(Me)_2$, $H_2BDC$—$(Cl)_2$, $H_2BDC$—$(COOH)_2$, $H_2BDC$—$(OC_3H_5)_2$, $H_2BDC$—$(OC_7H_7)_2$, $H_3BTC$, $H_3BTE$, $H_3BBC$, $H_4ATC$, $H_3THBTS$, $H_3ImDC$, $H_3BTP$, DTOA, $H_3BTB$, $H_3TATB$, $H_4ADB$, TIPA, ADP, $H_6BTETCA$, DCDPBN, BPP34C10DA, $Ir(H_2DPBPyDC)(PPy)_2^+$, $H_6DH_9PhDC$, $H_4DH11PhDC$, $H_6TPBTM$, $H_6BTEI$, $H_6BTPI$, $H_6BHEI$, $H_6BTTI$, $H_6PTEI$, $H_6TTEI$, $H_6BNETPI$, $H_6BHEHPI$, or HMeIM. The metal ions and the organic ligands described above may be formed into the metal-organic framework by a solvothermal synthesis method, a hydrothermal synthesis method, a microwave synthesis method, a ultrasonic synthesis method, a mechanochemical synthesis method, a dry-gel conversion method, a solvent-minimum synthesis method, an electrochemical synthesis method, or a fine fluid synthesis method. A structure of the metal-organic framework, a size of the molecular sieve, a size of a pore, and a size of the inner cavity may be adjusted according to kinds of the metal ion and the organic ligand.

In the step (b), various metal ions may be injected in the empty cavity of the metal-organic framework, and the injected metal ions may be reduced by a reducing agent to form the metal-organic framework in which the metal-organic framework is included. In particular, when the nanoparticle catalyst is formed using the metal-organic framework as a template, the quantity of the metal salt precursor inserted in the cavity of the metal-organic framework may be adjusted to adjust the size of the nanoparticle catalyst in a range of 0.1 nm to 10 nm. A kind and a shape of the metal salt substituted in the metal-organic framework may be very various. For example, a catalyst in a salt form may include at least one of, but not limited to, ruthenium(III) chloride, ruthenium acetate, iridium(III) chloride, iridium acetate, tantalum(V) chloride, palladium(II) chloride, copper(II) nitrate, copper(II) chloride, cobalt(II) nitrate, cobalt (II) acetate, lanthanum(III) nitrate, lanthanum(III) acetate, platinum(IV) chloride, platinum(II) acetate, gold(I, III) chloride, gold(III) acetate, silver chloride, silver acetate, iron(III) chloride, iron(III) acetate, nickel(II) chloride, or nickel(II) acetate. When the nanoparticle catalyst is synthesized by providing the metal salt into the inner cavity of the metal-organic framework, a nanoparticle metal catalyst may be inserted in the inner cavity of the unit metal-organic framework and the unit metal-organic frameworks may be gathered to form the metal-organic framework molecular sieve. Thus, the unit metal-organic frameworks and the nanoparticle catalysts may be well dispersed. In addition, an electrospinning solution including the metal-organic framework molecular sieve in which the nanoparticle catalysts are inserted in the inner cavities of the unit metal-organic frameworks may be electrospun by the electrospinning apparatus to synthesize the metal oxide precursor/polymer/metal-organic framework/nanoparticle catalyst complex nanofiber. Finally, to synthesize the porous semiconductor metal oxide complex nanofiber to which the nanoparticle catalysts are coupled, a high-temperature thermal treatment process should be performed. During the high-temperature thew al treatment process, the organic ligands of the metal-organic framework may be completely removed to synthesize the porous semiconductor metal oxide complex nanofiber to which pure metal or metal oxide nanoparticle catalysts are coupled.

The step (c) is step of manufacturing an electrospinning solution for performing the electrospinning process. In the step (c), a polymer and a metal precursor which act as a template for easily forming a nanofiber may be dissolved in a solvent to manufacture the electrospinning solution. In detail, the polymer may include at least one of poly(methyl methacrylate) (PMMA), polyvinyl pyrrolidone (PVP), poly (vinyl acetate) (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, or polyvinylidene fluoride. A representative metal salt may have an acetate form, a chloride form, an acetylacetonate form, a nitrate form, a methoxide form, an ethoxide form, a butoxide form, an isopropoxide form, or a sulfide form, which includes a metal salt. In addition, the metal-organic framework molecular sieve embedded with the nanoparticle catalysts, manufactured in the step (b), may be added into the electrospinning solution to manufacture the electrospinning solution. In the electrospinning solution, a concentration of the metal-organic framework molecular sieve embedded with the nanoparticle catalysts may be variously adjusted in a range of 0.001 wt % to 2 wt %. A content of the nanoparticle catalysts included in a heterojunction metal oxide may be adjusted according to the concentration of the metal-organic framework molecular sieve.

The step (c) may be step of synthesizing the metal-organic framwork/metal oxide precursor/polymer complex nanofiber using the electrospinning method, and the metal-organic framework molecular sieves including the nanoparticle catalysts may be uniformly distributed in the metal-organic framework/metal oxide precursor/polymer complex nanofiber because of the excellent dispersion of the metal-organic frameworks having the cavities in which the nanoparticle catalysts synthesized in the step (b) are formed.

In the step (d), the polymer included in the metal-organic framework/metal oxide precursor/polymer complex nanofiber may be decomposed and removed by the high-temperature thermal treatment to form fine pores in the nanofiber, and the metal oxide precursor and the metal ions of the metal-organic frameworks may be oxidized and crystallized by the high-temperature thermal treatment, thereby forming the porous semiconductor metal oxide complex nanofiber functionalized by the porous first metal oxide particles including the metal nanoparticle catalysts and uniformly coupled to the inside and the surface of the second metal oxide nanofiber. At this time, the first metal oxide particle means a metal oxide formed by oxidation of the metal ion of the metal-organic framework, and the second metal oxide nanofiber means a metal oxide nanofiber formed by oxidation of the metal salt dispersed together with the metal-organic framework in the electrospinning solution.

In the step (e), the porous semiconductor metal oxide complex nanofibers including the nanoparticle catalysts, obtained in the step (d), may be dispersed in a solvent, and then, the dispersion solution may be applied to a previously prepared sensor substrate (e.g., an alumina insulating substrate on which parallel electrodes capable of measuring variations of electrical conductivity and electrical resistance are formed) by a coating method such as, but not limited to, a drop coating method, a spin coating method, an ink-jet printing method, or a dispensing method.

In the step (f), the sensor array including two or more kinds of sensors including various kinds of nanoparticle catalyst-first metal oxide particle-second metal oxide complex nanofiber sensing members may be manufactured using a combination of different kinds of nanoparticle catalysts and different kinds of first metal oxide/second metal oxide complex nanofibers synthesized in the step (e).

A diameter of the manufactured porous semiconductor metal oxide complex nanofiber including the nanoparticle catalysts may range from 100 nm to 6 μm.

In the manufactured sensing member, the fine nanoparticle catalysts of 10 nm or less may be uniformly included in the inside and the outside of the porous semiconductor metal oxide complex nanofiber. Thus, characteristics of the catalyst may be maximized and sensitivity of the sensing member may also be maximized.

In the nanoparticle catalyst-first metal oxide particle-second metal oxide nanofiber complex sensing member manufactured by the above manufacturing method, a weight ratio of the nanoparticle catalyst may range from 0.001 wt % to 25 wt % with respect to a weight of the first metal oxide particle and may range from 0.001 wt % to 0.5 wt % with respect to a weight of the second metal oxide nanofiber. The complex sensing member according to some embodiments of the inventive concepts may sense specific gases included in the man's exhaled breath and may sense harmful environmental gases inside and outside a room.

BRIEF DESCRIPTION OF THE DRAWINGS

The inventive concepts will become more apparent in view of the attached drawings and accompanying detailed description.

DETAILED DESCRIPTION OF THE EMBODIMENTS

Figure 1:
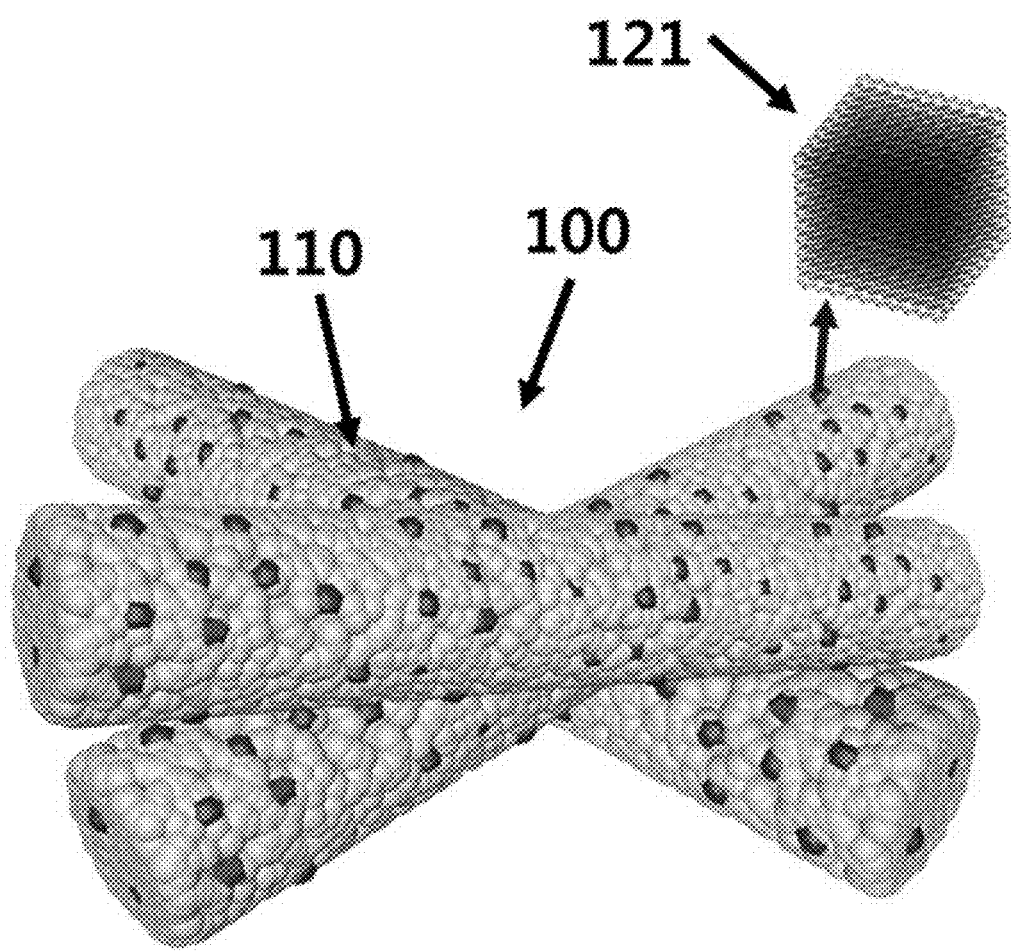
FIG. 1 is a schematic diagram illustrating a gas sensor member using a porous semiconductor metal oxide complex nanofiber functionalized by uniformly distributing porous first metal oxide particles including nanoparticle catalysts in an inside and on a surface of a second metal oxide nanofiber, according to some embodiments of the inventive concepts.

The inventive concepts will now be described more fully hereinafter with reference to the accompanying drawings, in which exemplary embodiments of the inventive concepts are shown.

In addition, in explanation of the present invention, the descriptions to the elements and functions of related arts may be omitted if they obscure the subjects of the present invention.

It will be also understood that although the terms first, second, third etc. may be used herein to describe various elements, these elements should not be limited by these terms. These terms are only used to distinguish one element from another element.

Hereinafter, a gas sensor member using a porous semiconductor metal oxide complex nanofiber functionalized by uniformly distributing porous first metal oxide particles, including metal nanoparticle catalysts synthesized using a metal-organic framework, in an inside and on a surface of a second metal oxide nanofiber, a gas sensor using the same, and a method of manufacturing the same will be described in detail with reference to the accompanying drawings.

According to some embodiments of the inventive concepts, nanoparticle catalysts having sizes ranging from 0.1 nm to 10 nm may be embedded in a metal-organic framework by a synthesis method, and the metal-organic framework in which the nanoparticle catalysts are embedded may be injected into an electrospinning solution. Porous first metal oxide particles may be coupled to an inside and a surface of a second metal oxide nanofiber to manufacture a sensing material for a gas sensor.

To improve characteristics of a gas sensor using a metal oxide, researches for using a metal or a metal oxide catalyst along with improvement of a specific surface area have been conducted. However, these researches should need both a process of increasing the specific surface area and a process of coupling a catalyst to a nanofiber. In particular, a process of synthesizing a metal or metal oxide nanoparticle catalyst having a size of several nm and a process of uniformly distributing the synthesized nano-sized nanoparticle catalysts into the inside of the nanofiber are quite complex.

To overcome these disadvantages, in some embodiments of the inventive concepts, nanoparticle catalysts may be inserted into an inner cavity of a unit metal-organic framework to easily synthesize the nanoparticle catalysts having sizes ranging from 0.1 nm to 10 nm, and the metal-organic frameworks having the nanoparticle catalysts may be mixed with a metal oxide precursor/polymer mixed spinning solution. Thereafter, an electrospinning process may be performed using the mixture solution to uniformly distribute and couple the metal-organic frameworks having the nanoparticle catalysts to a surface and an inside of a metal oxide precursor/polymer complex nanofiber. Next, a high-temperature thermal treatment process may be performed to remove organic ligands of the metal-organic frameworks and polymer included in the nanofiber, thereby forming a porous semiconductor metal oxide complex nanofiber including the nanoparticle catalysts. Thus, a sensing material in which the nanoparticle catalysts are uniformly dispersed without aggregation may be synthesized in large quantities.

Here, the porous semiconductor metal oxide complex nanofiber having the inside and the outside at which the nanoparticle catalysts are uniformed distributed may maximize a catalyst effect shown in reaction between the sensing material and gases since the nanoparticle catalysts are uniformly distributed. In addition, a metal ion of the metal-organic framework and the metal oxide precursor are oxidized to form the first metal oxide particle and the second metal oxide nanofiber, respectively. A heterojunction between the first metal oxide particle and the second metal oxide nanofiber may show properties of a new synthesis material, not properties of a single metal oxide. Thus, the porous semiconductor metal oxide complex nanofiber having the uniformly distributed nanoparticle catalysts may correspond to a new material and may have higher sensitivity than a conventional semiconductor nanofiber. In particular, various metal or metal oxide nanoparticle catalysts having sizes of 0.1 nm to 10 nm may be synthesized in the inner cavity of the unit metal-organic framework, and thus a gas sensor having selectivity with respect to a specific gas may be manufactured. To manufacture the member for a gas sensor having the characteristics described above, embodiments of the inventive concepts may provide a member for a gas sensor, a gas sensor, and a method of manufacturing the same.

FIG. 1 is a schematic diagram illustrating a member 100 for a gas sensor, which uses a porous semiconductor metal oxide complex nanofiber 110 including nanoparticle catalysts 121, according to some embodiments of the inventive concepts. In FIG. 1, the member 100 for a gas sensor is formed using the porous semiconductor metal oxide complex nanofiber 100. However, embodiments of the inventive concepts are not limited thereto. In certain embodiments, another kind of a member for a gas sensor may be formed using a nano-structure such as a nanotube or a nanorod shape.

When a high-temperature thermal treatment process is performed on a complex nanofiber manufactured by electrospinning the metal oxide precursor/polymer mixed spinning solution and the metal-organic framework having the cavity embedded with the nanoparticle catalysts, a metal ion of the metal-organic framework and the metal oxide precursor are oxidized to form a first metal oxide particle and a second metal oxide nanofiber forming a heterojunction, and organic ligands of the metal-organic framework and the polymer may be removed. Thus, the porous semiconductor metal oxide complex nanofiber may be formed.

Here, metals synthesized in the cavity of the unit metal-organic framework include a metal that can exist in an ion state and are not limited to a specific metal. For example, the metals may be obtained using at least one precursor of copper(II) nitrate, copper(II) chloride, cobalt(II) nitrate, cobalt(II) acetate, lanthanum(III) nitrate, lanthanum(III) acetate, platinum(IV) chloride, platinum(II) acetate, gold(I, III) chloride, Gold(III) acetate, silver chloride, silver acetate, iron(III) chloride, iron(III) acetate, nickel(II) chloride, nickel(II) acetate, ruthenium(III) chloride, ruthenium acetate, iridium(III) chloride, iridium acetate, tantalum(V) chloride, or palladium(II) chloride. The nanoparticle catalyst such as Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, and/or Ge may be synthesized using the precursor. The amount of the precursor may be adjusted to adjust sizes of the nanoparticle catalysts in a range of 0.1 nm to 10 nm by using the metal-organic framework. Since the nanoparticle catalysts are embedded in the cavities of the unit metal-organic frameworks of a metal-organic framework molecular sieve, the nanoparticle catalysts may not be aggregated in the electrospinning solution but may be well dispersed in the electrospinning solution.

Roles of nanoparticle catalysts acting in a gas sensor sensing material will be described in detail hereinafter. A nanoparticle catalyst including a noble metal (e.g., platinum (Pt) or gold (Au)) may show a chemical sensitization effect that increases a concentration of adsorption oxygen ions used in surface reaction by accelerating decomposition reaction of oxygen molecules between a surface of a metal oxide and an air layer. Another nanoparticle catalyst (e.g., PdO, $Co_3O_4$, NiO, $Cr_2O_3$, CuO, $Fe_2O_3$, $Fe_3O_4$, $TiO_2$, ZnO, $SnO_2$, $V_2O_5$, or $V_2O_3$) affecting improvement of a sensing characteristic may show an electronic sensitization effect that causes catalytic reaction through an oxidation process.

Since the nanoparticle catalysts 121 synthesized using the metal-organic framework described above are embedded in the cavity of the unit metal-organic framework, the nanoparticle catalysts 121 may be well dispersed without aggregation, unlike nanoparticle catalysts synthesized by a general polyol process method. Due to these features, when the metal-organic frameworks embedded with the nanoparticle catalysts are added into the metal oxide precursor/polymer mixed spinning solution and the mixture solution is spun, the metal-organic frameworks in which the nanoparticle catalysts are uniformly dispersed may be uniformly coupled to the inside and the outside of the metal oxide precursor/polymer nanofiber.

The metal ions of the metal-organic frameworks and the metal oxide precursors may be oxidized to form the first metal oxide/second metal oxide heterojunction in the process of removing the organic ligands of the metal-organic frameworks and the polymer by the high-temperature treatment process (e.g., 400☐ to 800☐) having a heating rate of 5☐/min.

The metal oxide formed by oxidizing the metal ion of the metal-organic framework may include at least one of ZnO, $Fe_2O_3$, $Fe_3O_4$, NiO, CuO, $In_2O_3$, $Co_3O_4$, $NiCo_2O_4$, $ZrO_2$, $Cr_3O_4$, $MnO_2$, or MgO. In addition, the semiconductor metal oxide nanofiber including the nano-structure includes a material of which an electrical resistance and conductivity are changeable by adsorption and detachment of a gas. For example, the semiconductor metal oxide nanofiber including the nanostructure may include at least one of, but not limited to, ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $V_2O_5$, $Cr_2O_3$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, or $Ba_{0.5}Sr_{0.5}Co_{0.8}Fe_{0.2}O_{3-7}$.

Since a sensor having high sensitivity and high selectivity with respect to a specific gas is realized using the member 100 forming using the porous semiconductor metal oxide complex nanofiber 110 including the nanoparticle catalysts 121, the sensor may sense the specific gas acting as a biomarker in exhaled breath of a human body to early diagnose a disease of the human body and may be applied as an environmental sensor capable of monitoring harmful environmental gases. In addition, the amount of the nanoparticle catalysts coupled to the nanofiber may be quantitatively adjusted to effectively adjust the catalyst characteristic. Furthermore, various kinds of the first metal oxide/second metal oxide heterojunction complexes may be formed to easily and rapidly manufacture members sensing various kinds of gases.

Figure 2:
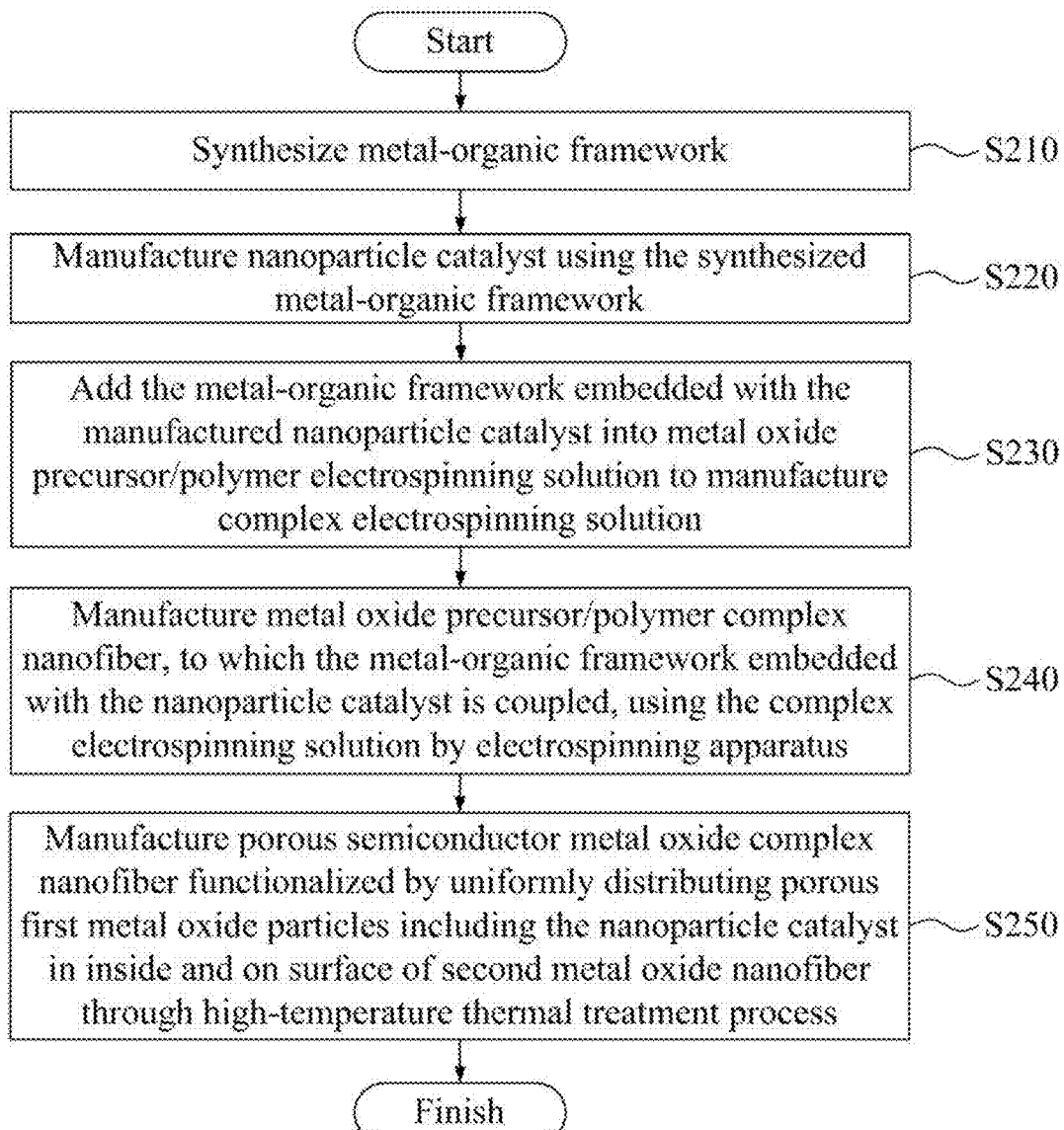
FIG. 2 is a flowchart illustrating a method of manufacturing a gas sensor using a porous semiconductor metal oxide complex nanofiber functionalized by uniformly distributing porous first metal oxide particles including nanoparticle catalysts in an inside and on a surface of a second metal oxide nanofiber, according to some embodiments of the inventive concepts.

FIG. 2 is a flow chart illustrating a method of manufacturing a member for a gas sensor by using a porous semiconductor metal oxide complex nanofiber including nanoparticle catalysts through an electrospinning method, according to some embodiments of the inventive concepts. As shown in the flow chart of FIG. 2, the method of manufacturing a member for a gas sensor may include synthesizing metal-organic frameworks (S210), manufacturing nanoparticle catalysts using the synthesized metal-organic frameworks (S220), manufacturing a complex electrospinning solution by adding the metal-organic frameworks, in which the manufactured nanoparticle catalysts are embedded, into a metal oxide precursor/polymer electrospinning solution (S230), manufacturing a metal oxide precursor/polymer complex nanofiber, to which the metal-organic frameworks embedded with the nanoparticle catalysts are coupled, by an electrospinning apparatus using the complex electrospinning solution (S240), and manufacturing a porous semiconductor metal oxide complex nanofiber functionalized by uniformly distributing porous first metal oxide particles including the nanoparticle catalysts in an inside and on a surface of a second metal oxide nanofiber through a high-temperature thermal treatment (S250). Hereinafter, the steps will be described in more detail.

First, the step S210 of synthesizing the metal-organic frameworks will be described.

The metal-organic framework synthesized in the step S210 may be a porous material formed by metal ions and organic ligands combined with the metal ions and may have at least one of various structures based on a kind thereof. In general, the metal-organic framework may have a globe shape of which an inside is empty. An inner pore of the metal-organic framework may range from 0.9 nm to 30 nm and may have one of various sizes according to a kind of the metal-organic framework. For example, an outside diameter of the metal-organic framework may range from 20 nm to 2 μm. The unit metal-organic frameworks may be gathered to form a nano metal-organic framework molecular sieve having a size of several tens nanometers or a bulk metal-organic framework molecular sieve having a size of several micrometers. In some embodiments, the metal-organic framework according to the inventive concepts may include a metal-organic framework having an inner cavity in which metal ions can be embedded. The metal-organic framework according to the inventive concepts may be, but not limited to, ZIF-1, ZIF-2, ZIF-3, ZIF-4, ZIF-5, ZIF-6, ZIF-7, ZIF-8, ZIF-9, ZIF-10, ZIF-11, ZIF-12, ZIF-22, ZIF-65, ZIF-69, ZIF-71, ZIF-78, ZIF-90, ZIF-95, ZIF-9-67, or SIM-1. In addition, a metal salt used to form the metal-organic framework may include at least one of, but not limited to, $Zn_4O(CO_2)_6$, $Zn_3O(CO_2)_6$, $Cr_3O(CO_2)_6$, $In_3O(CO_2)_6$, $Ga_3O(CO_2)_6$, $Cu_2O(CO_2)_4$, $Zn_2O(CO_2)_4$, $Fe_2O(CO_2)_4$, $Mo_2O(CO_2)_4$, $Cr_2O(CO_2)_4$, $Co_2O(CO_2)_4$, $Ru_2O(CO_2)_4$, $Zr_6O_4(OH)_4$, $Zr_6O_4(CO_2)_{12}$, $Zr_6O_4(CO_2)_8$, $In(C_5HO_4N_2)_4$, $Na(OH)_2(SO_3)_3$, $Cu_2(CNS)_4$, $Zn(C_3H_3N_2)_4$, $Ni_4(C_3H_3N_2)_8$, $Zn_3O_3(CO_2)_3$, $Mg_3O_3(CO_2)_3$, $Co_3O_3(CO_2)_3$, $Ni_3O_3(CO_2)_3$, $Mn_3O_3(CO_2)_3$, $Fe_3O_3(CO_2)_3$, $Cu_3O_3(CO_2)_3$, $Al(OH)(CO_2)_2$, $VO(CO_2)_2$, $Zn(NO_3)_2$, $Zn(O_2CCH_3)$, $Co(NO_3)_2$, or $Co(O_2CCH_3)$. Organic ligands used to form the metal-organic framework may include at least one of, but not limited to, oxalic acid, fumaric acid, $H_2BDC$, $H_2BDC$—Br, $H_2BDC$—OH, $H_2BDC$—$NO_2$, $H_2BDC$—$NH_2$, $H_4DOT$, $H_2BDC$-$(Me)_2$, $H_2BDC$—$(Cl)_2$, $H_2BDC$—$(COOH)_2$, $H_2BDC$—$(OC_3H_5)_2$, $H_2BDC$—$(OC_7H_7)_2$, $H_3BTC$, $H_3BTE$, $H_3BBC$, $H_4ATC$, $H_3THBTS$, $H_3ImDC$, $H_3BTP$, DTOA, $H_3BTB$, $H_3TATB$, $H_4ADB$, TIPA, ADP, $H_6BTETCA$, DCD-PBN, BPP34C10DA, $Ir(H_2DPBPyDC)(PPy)_2^+$, $H_4DH_9PhDC$, $H_4DH11PhDC$, $H_6TPBTM$, $H_6BTEI$, $H_6BTPI$, $H_6BHEI$, $H_6BTTI$, $H_6PTEI$, $H_6TTEI$, $H_6BNETPI$, $H_6BHEHPI$, or HMeIM. Embodiments of the inventive concepts are not limited to a specific metal ion or a specific organic ligand. The metal ions and the organic ligands may be combined with each other by at least one of a room-temperature synthesis method, a hydrothermal synthesis method, a solvothermal synthesis method, an ionothermal synthesis method, a sonochemical synthesis method, a solvent-minimum synthesis method, or a mechanochemical synthesis method, thereby synthesizing the metal-organic frameworks.

Next, the step S220 of manufacturing the nanoparticle catalysts using the synthesized metal-organic frameworks will be described.

The metal-organic frameworks are immersed in a solution, in which the metal salt is dissolved, for a time of 1 hour to 24 hours to sufficiently diffuse the metal salt into inner spaces of the synthesized metal-organic frameworks. A concentration (e.g., a salt concentration) of the solution containing the metal-organic frameworks may range from 0.1 mg/ml to 200 mg/ml. A solvent used to form the metal salt solution may include a solvent capable of dissolving the metal salt. In some embodiments, the solvent used to form the metal salt solution may include at least one selected from commercial solvents such as, but not limited to, ethanol, deionized (DI) water, chloroform, N,N'-dimethylformamide, dimethylsulfoxide, N,N'-dimethylacetamide, and N-methylpyrrolidone. When the metal salt embedded in the cavity of the metal-organic framework has a precursor shape in an ion state, a kind and a shape of the metal salt are not limited to a specific kind and a specific shape. The metal salt may be a salt-type precursor capable of providing at least one of Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, or Ge into the metal-organic framework. After the high-temperature thermal treatment, the organic ligands of the metal-organic frameworks may be removed and the nanoparticle catalysts may be changed into metal or metal oxide catalyst particles. At this time, a metal particle which can be easily oxidized may be easily changed into a metal oxide particle. The metal oxide particle may have an N-type or P-type semiconductor characteristic. A reducing agent that reduces the metal salt included in the cavity of the metal-organic framework to form a metal nanoparticle catalyst may include at least one of, but not limited to, sodium borohydride ($NaBH_4$), formic acid (HCOOH), oxalic acid ($C_2H_2O_4$), or lithium aluminum hydride ($LiAlH_4$). The metal-organic frameworks including the nanoparticle catalysts may be extracted using a centrifugal machine from the solution in which the metal salts in the metal-organic frameworks are reduced using the reducing agent. At this time, a rotation speed of the centrifugal machine may range from about 10,000 rpm to about 13,000 rpm.

Next, the step S230 of manufacturing the metal oxide precursor/polymer complex electrospinning solution including the metal nanoparticle catalysts synthesized using the synthesized metal-organic frameworks will be described in detail.

The metal oxide precursor/polymer complex electrospinning solution in which the above manufactured metal-organic frameworks including the nanoparticle catalysts are uniformly dispersed may be manufactured in the step S230. Here, a solvent is capable of dissolving the metal oxide precursor and the polymer. For example, the solvent may include at least one selected from commercial solvents such as N,N'-dimethylformamide, dimethylsulfoxide, N,N'-dimethylacetamide, N-methylpyrrolidone, DI water, and ethanol. In addition, the polymer used here may be a polymer that is dissolvable together with the solvent and is removable by the high-temperature thermal treatment. For example, the polymer used in the step S230 may include at least one of poly(methyl methacrylate) (PMMA), polyvinyl pyrrolidone (PVP), poly(vinyl acetate) (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, or polyvinylidene fluoride.

The metal oxide precursor used in the step S230 may include a precursor capable of forming a semiconductor metal oxide nanofiber having a gas sensor characteristic. For example, the metal oxide precursor used in the step S230 may include at least one of, but not limited to, $SnO_2$, $WO_3$, $CuO$, $NiO$, $ZnO$, $Zn_2SnO_4$, $CO_3O_4$, $Cr_2O_3$, $LaCoO_3$, $V_2O_5$, $IrO_2$, $TiO_2$, $Er_2O_3$, $Tb_2O_3$, $Lu_2O_3$, $Ag_2O$, $SrTiO_3$, $Sr_2Ta_2O_7$, $BaTiO_3$, or $Ba_{0.5}Sr_{0.5}Co_{0.8}Fe_{0.2}O_{3-7}$.

A ratio of the polymer:the metal oxide precursor may range from 1:0.5 to 1:2, and a ratio of the polymer:the nanoparticle catalysts synthesized using the metal-organic frameworks may range from 1:0.00001 to 1:0.1. The kind of the metal salt embedded in the metal-organic framework may be selected in due consideration of a sensing characteristic and selectivity of a gas to be sensed, and the gas sensor members having various characteristics may be manufactured by changing the metal salt.

A process of manufacturing the electrospinning solution in the step S230 will be described hereinafter. The metal oxide precursor may be dissolved in the solvent to form a solution, and then, the previously manufactured metal-organic framework solution including the nanoparticle catalysts may be added into the solution. The solutions may be mixed with each other to uniformly disperse the metal-organic frameworks including the nanoparticle catalysts. After sufficiently mixing the solutions, the polymer may be added into the mixed solution at a moderate rate. The solution including the polymer, the metal oxide precursor, and the metal-organic frameworks may be stirred until the polymer is completely dissolved in the solution. The solution may be stirred a temperature ranging from room temperature to 50□ and may be sufficiently stirred for a time of 5 hours to 48 hours. Thus, the metal-organic frameworks including the nanoparticle catalysts, the metal oxide precursor, and the polymer may be uniformly mixed with each other in the solution. This solution may correspond to the complex electrospinning solution. The synthesized complex electrospinning solution may be electrospun to manufacture the metal oxide precursor/polymer complex nanofiber to which the metal-organic frameworks including the nanoparticle catalysts are coupled (S240).

In the step S240 performed by the electrospinning method, a syringe may be filled with the metal oxide precursor/polymer complex electrospinning solution including the metal-organic frameworks including the nanoparticle catalysts, and then, the syringe may be pushed at a certain rate by a syringe pump to discharge a certain amount of the electrospinning solution. An electrospinning system may include a high-voltage device, a grounded conductive substrate, the syringe, and a syringe needle. A high voltage of 5 kV to 30 kV may be applied between the solution filling the syringe and the conductive substrate to generate an electric field, and the electrospinning solution discharged through the syringe needle by the electric field may be electrospun to be lengthily pulled out in a nanofiber form. The solvent included in the electrospinning solution lengthily pulled out may be evaporated and volatilized to obtain a solid polymer fiber. At this time, the metal oxide precursor and the metal-organic frameworks including the nanoparticle catalysts may be included in the solid polymer fiber. In other words, the complex fiber containing the metal oxide precursor and the metal-organic frameworks including the nanoparticle catalysts is manufactured. A discharging rate of the electrospinning solution may be adjusted in a range of 0.01 ml/min to 0.5 ml/min. The complex nanofiber including the metal oxide precursor, the polymer, and the metal-organic frameworks including the nanoparticle catalysts may have a desired diameter by adjusting the voltage and a discharging amount of the electrospinning solution.

Lastly, in the step S250 of manufacturing the porous semiconductor metal oxide complex nanofiber functionalized by uniformly distributing the first metal oxide particles, in which the nanoparticle catalysts are uniformly included without aggregation, in the inside and on the surface of the second metal oxide nanofiber through the high-temperature thermal treatment of the manufactured complex nanofiber, the polymer and the organic ligands of the metal-organic frameworks may be decomposed and removed by the thermal treatment performed at a temperature of 400□ to 800□. In addition, the metal ions of the metal-organic frameworks may be oxidized to form the first metal oxide particles during the thermal treatment, and the metal oxide precursor may be oxidized to form the second metal oxide nanofiber during the thermal treatment. Thus, the semiconductor metal oxide complex nanofiber may be manufactured.

Figure 3:
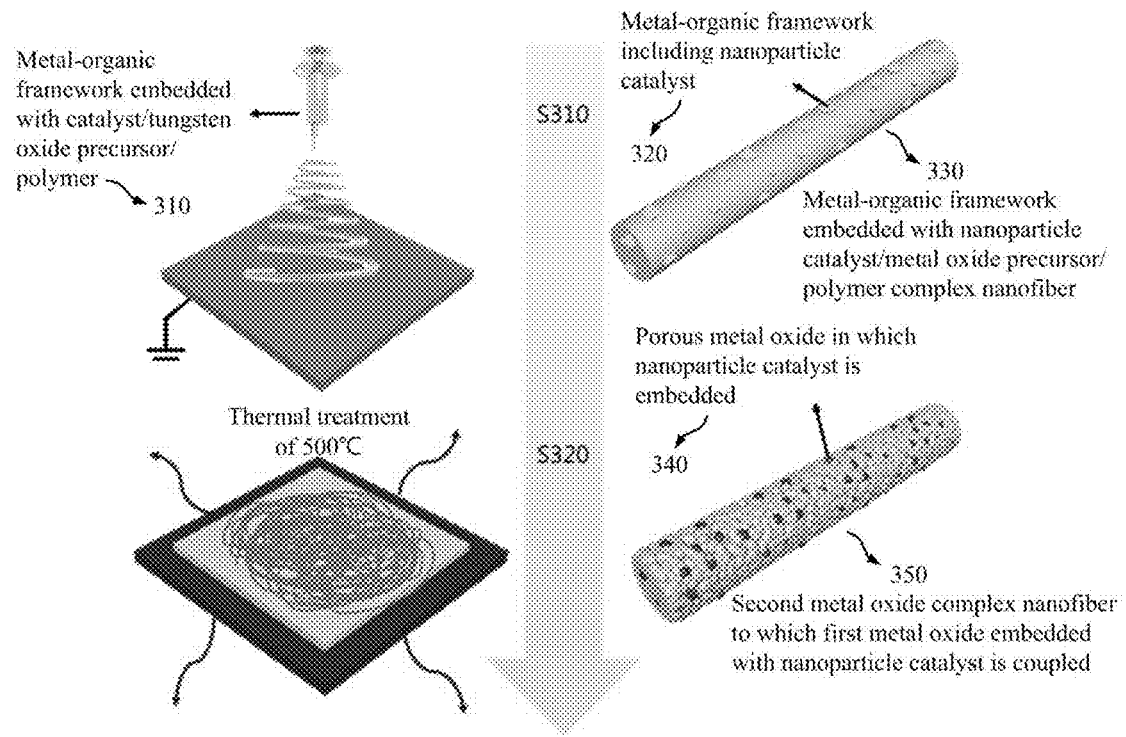
FIG. 3 is a schematic diagram illustrating a process of manufacturing a porous semiconductor metal oxide complex nanofiber functionalized by uniformly distributing porous first metal oxide particles including nanoparticle catalysts in the inside and on a surface of a second metal oxide nanofiber by using an electrospinning method, according to some embodiments of the inventive concepts.

FIG. 3 schematically illustrates a process order of manufacturing a semiconductor metal oxide/metal oxide complex nanofiber including the nanoparticle catalysts by using an electrospinning method, according to some embodiments of the inventive concepts.

First step S310 shows an embodiment of manufacturing a complex nanofiber using a complex electrospinning solution 310 including the metal oxide precursor, the polymer, and the metal-organic frameworks embedded with the nanoparticle catalysts by an electrospinning method. Metal-organic frameworks 320 including the nanoparticle catalysts are uniformly dispersed in a nanofiber 330 shown in FIG. 3 and manufactured by the above process.

Second step S320 shows a process of thermally treating the complex nanofiber synthesized in the step S310 at a high temperature. The thermal treatment is performed to 500□ at a heating rate of 5□/min, and thus the polymer and the organic ligands of the metal-organic frameworks are removed together and the metal oxide precursor and the metal ions of the metal-organic frameworks may be oxidized to synthesize a first metal oxide 340/second metal oxide complex nanofiber 350.

In the embodiment of FIG. 3, a ZnO/WO$_3$ complex nanofiber is manufactured using zinc metal ions and tungsten oxide. However, embodiments of the inventive concepts are not limited thereto. In certain embodiments, the metal ions and the metal oxide precursor may include one of the metal salts described above as examples.

According to the method of manufacturing the gas sensor member using the porous semiconductor metal oxide complex nanofiber 110 including the nanoparticle catalysts 121 by the electrospinning method in the above mentioned embodiments of the inventive concepts, a one-dimensional (D) nanofiber may be formed to have a wide surface area reacting with a gas and, at the same time, the catalysts having the chemical/electronic sensitization effect may be uniformly distributed in and on the 1D nanofiber. In addition, response rate, sensitivity, and selectivity characteristics of the gas sensor may be greatly improved by the heterojunction of the first metal oxide and the second metal oxide of which kinds are different from each other.

Hereinafter, embodiments of the inventive concepts will be described in detail with reference to embodiment examples and comparison examples. The embodiment examples and the comparison examples are used to explain the inventive concepts. However, embodiments of the inventive concepts are not limited to the following embodiment examples.

Embodiment Example 1: Manufacture of Metal-Organic Framework (Zeolitic Imidazolate Framework (ZIF-8)) in which Pd Nanoparticle Catalysts are Embedded To synthesize ZIF-8 corresponding to a kind of the metal-organic framework, 2.933 g of $Zn(NO_3)_2 \cdot H_2O$ corresponding to a zinc (Zn) precursor to be used for metal ions of the metal-organic framework and 6.489 g of 2-methylimidazole to be used for organic ligands of the metal-organic framework are dissolved in 200 mL of methanol to manufacture two solutions, respectively. After the two materials are completely dissolved in the two solutions, the two solutions are mixed with each other and then the mixed solution is stirred at room temperature at 200 rpm. After the mixed solution of which a color is changed into a milk color by the stirring process is precipitated for 24 hours at room temperature, the precipitated solution is cleaned using ethanol. Thereafter, residual organic ligands which do not react with the metal salt precursor are removed using a centrifugal machine. The centrifugal machine may be operated at 4,000 rpm for 10 minutes or more. After the ethanol cleaning process and the centrifugal process are further performed two times or more, purified ZIF-8 particles are dried at 50□ for 6 hours and are then collected.

Figure 4:
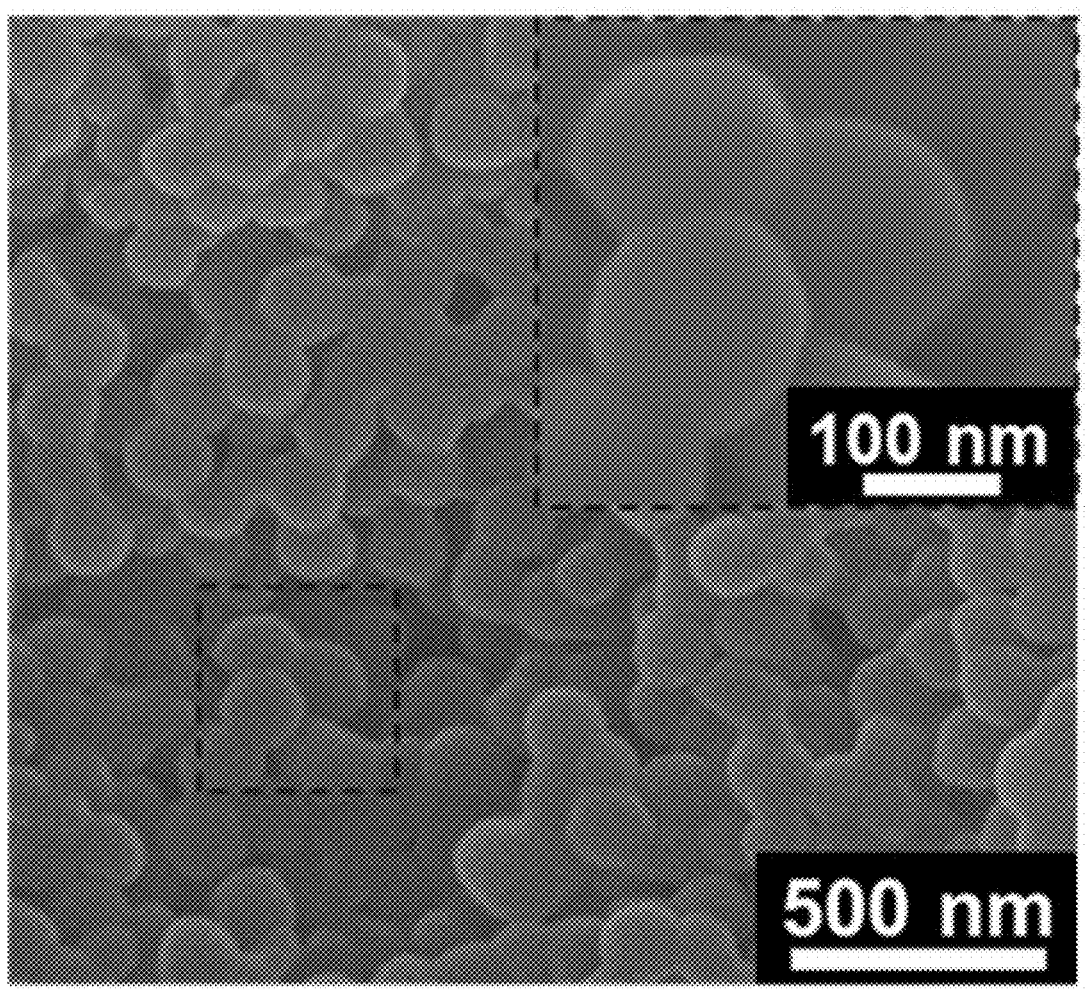
FIG. 4 is a scanning electron microscope (SEM) image showing a metal-organic framework ZIF-8 consisting of zinc metal ions ($Zn^{2+}$) and organic ligands (2-methylimidazole), according to an embodiment example 1 of the inventive concepts.

FIG. 4 is a SEM image showing the metal-organic framework ZIF-8 consisting of zinc metal ions ($Zn^{2+}$) and organic ligands (2-methylimidazole), which is manufactured by the above processes. It is recognized that the synthesized ZIF-8 has a size of about 100 nm.

The following processes are performed to embed a Pd nanoparticle catalyst in the metal-organic framework ZIF-8 which has a cavity and is synthesized by the above mentioned processes. $K_2PdCl_4$ is used as a Pd precursor necessary to synthesize the Pd nanoparticle catalyst. 10 mg of $K_2PdCl_4$ is dissolved in DI water (1 g) to prepare a water solution. Next, 40 mg of ZIF-8 is dissolved in DI water. A metal-organic framework solution is stirred while slowly providing the metal salt water solution formed as described above into the metal-organic framework solution, and thus Pd metal salts are diffused and embedded in cavities of a unit metal-organic framework. Here, the stirring process is performed at 100 rpm for about one hour at room temperature. After the metal salts are sufficiently embedded in the unit metal-organic framework, metal ions ($Pd^{2+}$) located in the cavities of the metal-organic frameworks are reduced to metal (Pd) by using a $NaBH_4$ reducing agent, thereby forming nanoparticle catalysts. The $NaBH_4$ reducing agent used at this time is prepared in a water solution form having a concentration of 40 mM, and 0.5 ml of the $NaBH_4$ reducing agent is added.

The metal-organic framework water solution including the Pd nanoparticle catalysts, which is manufactured by the above method, contains ligands existing together with the Pd metal salts and the reducing agent, and thus only the metal-organic frameworks including the synthesized metal nanoparticle catalysts are extracted using a centrifugal machine. The centrifugal machine may be operated at a rotation rate of 10,000 rpm to 12,000 rpm, and the centrifugal process may be performed for 10 minutes or more. The metal-organic frameworks including the Pd nanoparticle catalysts, which are extracted by the centrifugal machine, are dispersed again in water to finally prepare a water solution in which the Pd nanoparticle catalysts are dispersed in the metal-organic frameworks.

Figure 5:
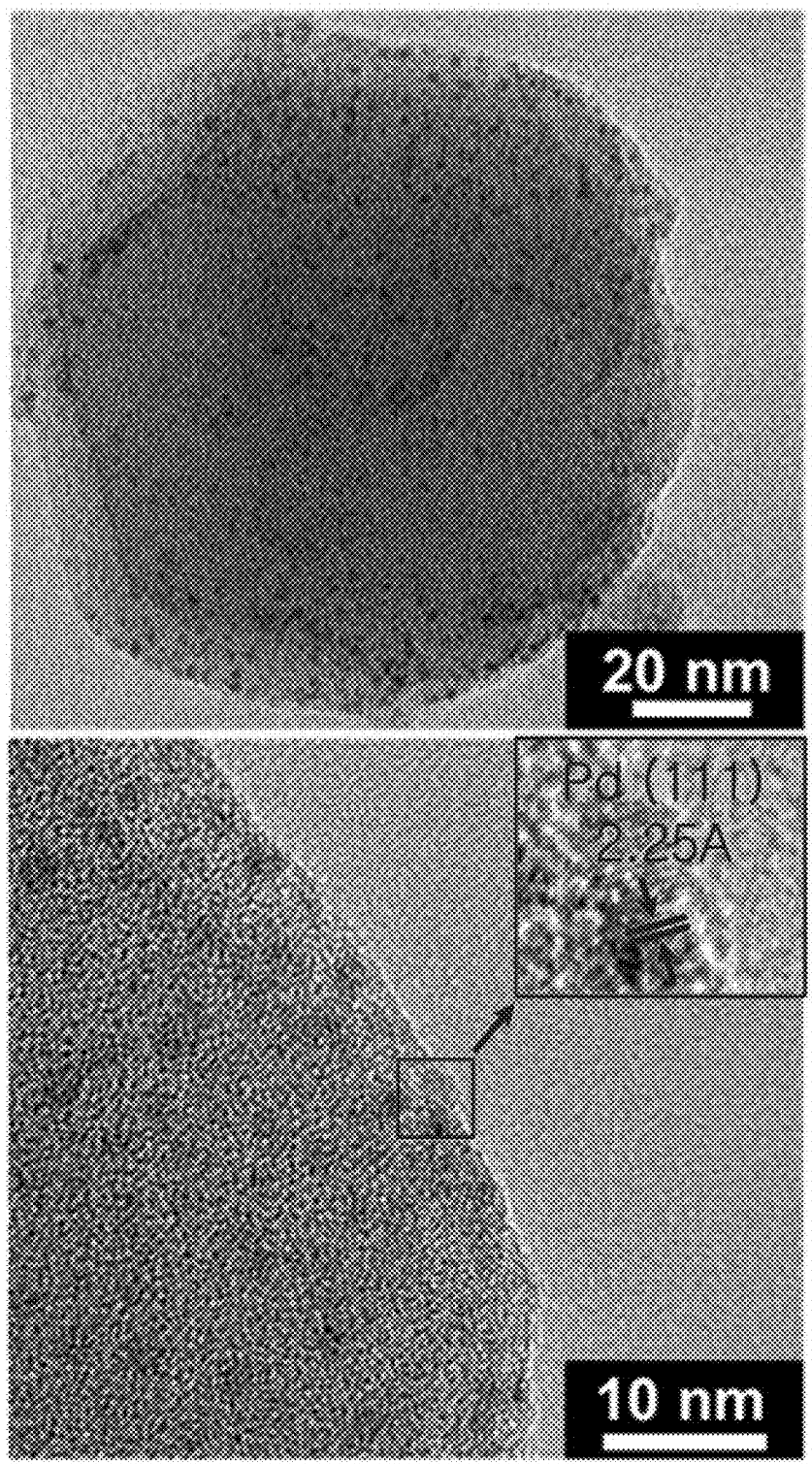
FIG. 5 is a transmission electron microscope (TEM) image showing the metal-organic framework ZIF-8 including a Pd nanoparticle catalyst, according to the embodiment example 1 of the inventive concepts.

FIG. 5 is a TEM image showing the metal-organic framework including the Pd nanoparticle catalyst, which is prepared by the above mentioned processes. It is recognized that the synthesized Pd nanoparticle catalyst has a size of 1 nm to 5 nm and a size of the metal-organic framework is about 100 nm.

Embodiment Example 2: Manufacture of Zinc Oxide (ZnO) Including PdO Catalyst/Tungsten Oxide ($WO_3$) Complex Nanofiber 330 by Using Metal-Organic Framework ZIF-8 Embedded with Pd Nanoparticle Catalyst 0.4 g of ammonium metatungstate hydrate (AMH) corresponding to the tungsten oxide precursor is added and dissolved in 3 g of DI water at room temperature. Next, 200 mg of the water solution including the metal-organic frameworks embedded with the Pd nanoparticle catalysts, which is manufactured in the embodiment example 1, is added into and mixed with the tungsten oxide precursor water solution. To smoothly perform an electrospinning process by increasing viscosity of the mixed solution, 0.5 g of a polyvinylpyrrolidone (PVP) polymer having a molecular weight of about 1,300,000 g/mol is added into the mixed solution, and the mixed solution including the PVP polymer is stirred at room temperature for 5 hours at 500 rpm to prepare an electrospinning solution. The prepared electrospinning solution is provided in a syringe (Henke-Sass Wolf, 10 mL NORM-JECT®), and the syringe is connected to a syringe pump to discharge the electrospinning solution at a discharging rate of 0.1 ml/min. 15 kV is applied between a needle (21 gauge) used in the electrospinning process and a collector collecting nanofibers to perform the electrospinning process. A stainless use steel (SUS) plate was used as the collector of the nanofibers, and a distance between the needle and the collector was 15 cm.

Figure 6:
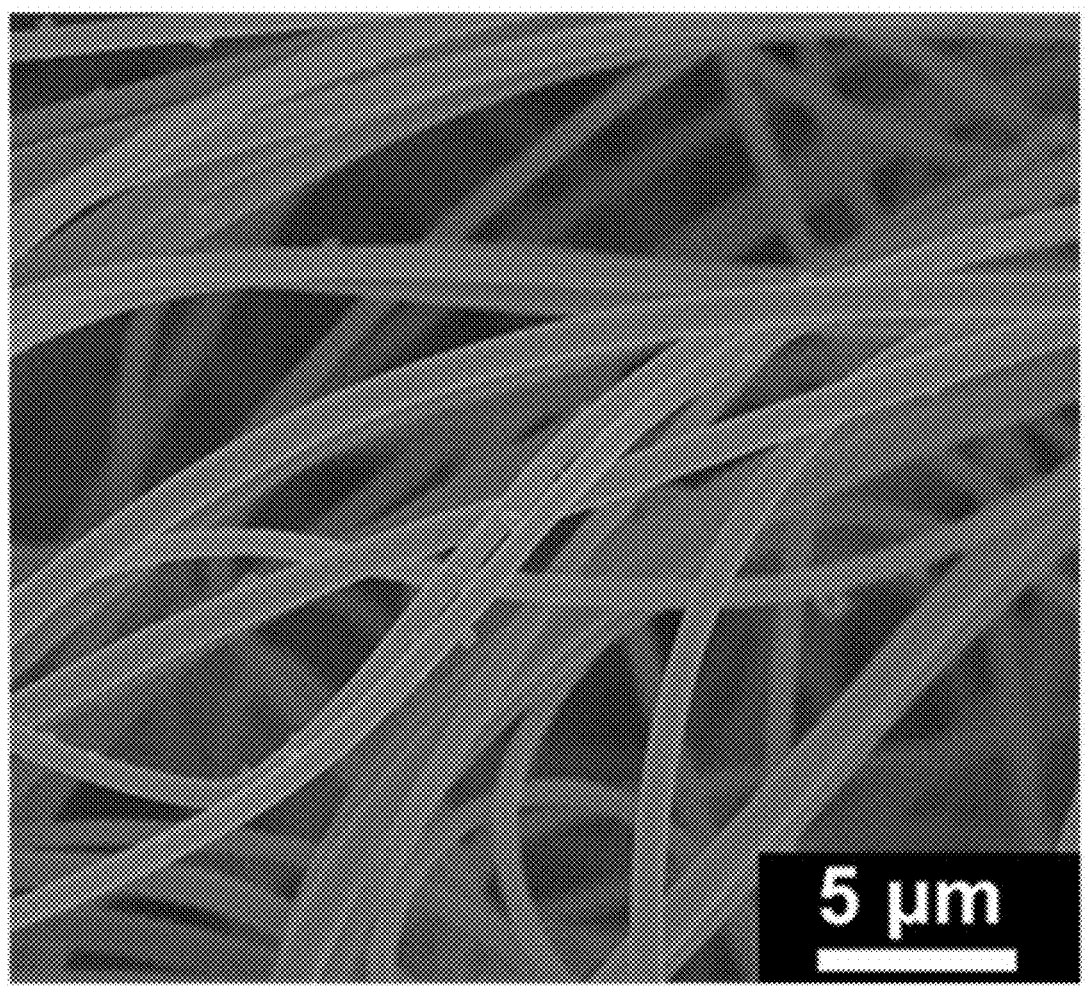
FIG. 6 is a SEM image showing a polymer complex nanofiber including a metal-organic framework ZIF-8 having a Pd nanoparticle catalyst, a tungsten oxide precursor, and polyvinylpyrrolidone (PVP), which is obtained after an electrospinning process according to an embodiment example 2 of the inventive concepts.

FIG. 6 is a SEM image showing the complex nanofiber including the metal-organic frameworks including the Pd nanoparticle catalysts, the tungsten oxide precursor, and the polymer, which is obtained after the electrospinning process. It is recognized that 1D nanofibers are synthesized and diameters of the 1D nanofibers range from 400 nm to 600 nm.

The complex nanofiber including the metal-organic frameworks including the Pd nanoparticle catalysts, the tungsten oxide precursor, and the polymer was heated to 500 at a heating rate of 4□/min and was then maintained at 500□ for an hour. Subsequently, the complex nanofiber was cooled to room temperature at a cooling rate of 40□/min. The thermal treatment was performed in air atmosphere by the Vulcan 3-550 small electric furnace of the Ney company. The organic ligands of the metal-organic frameworks and the polymer are decomposed and removed by the high-temperature thermal treatment process. In addition, since the thermal treatment process is performed in the air atmosphere, the metal ions ($Zn^{2+}$) of the metal-organic frameworks and the tungsten oxide precursor are oxidized to form ZnO and $WO_3$, respectively. The Pd nanoparticle catalysts embedded in the metal-organic frameworks are also oxidized to form PdO. Thus, a PdO—ZnO—$WO_3$ complex nanofiber, in which ZnO particles including the PdO nanoparticle catalysts are coupled to the inside and outside of the nanofiber, is formed.

Figure 7:
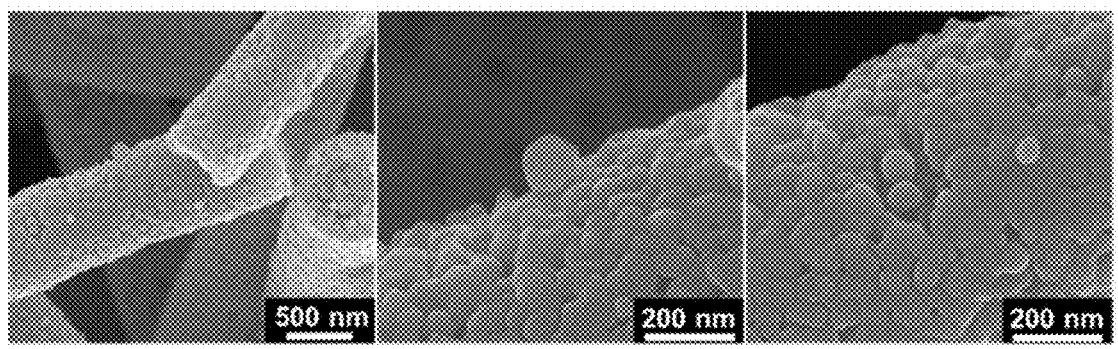
FIG. 7 is a SEM image showing a porous semiconductor metal oxide complex nanofiber functionalized by uniformly distributing porous ZnO particles including PdO nanoparticle catalysts in an inside and on a surface of a $WO_3$ nanofiber, which is obtained after a thermal treatment according to the embodiment example 2 of the inventive concepts.

FIG. 7 is a SEM image showing the $WO_3$ complex nanofiber to which ZnO including the PdO nanoparticle catalyst is coupled, which is obtained after the thermal treatment in the embodiment example 2. A diameter of the obtained complex nanofiber has a value between 400 nm to 600 nm.

Figure 8:
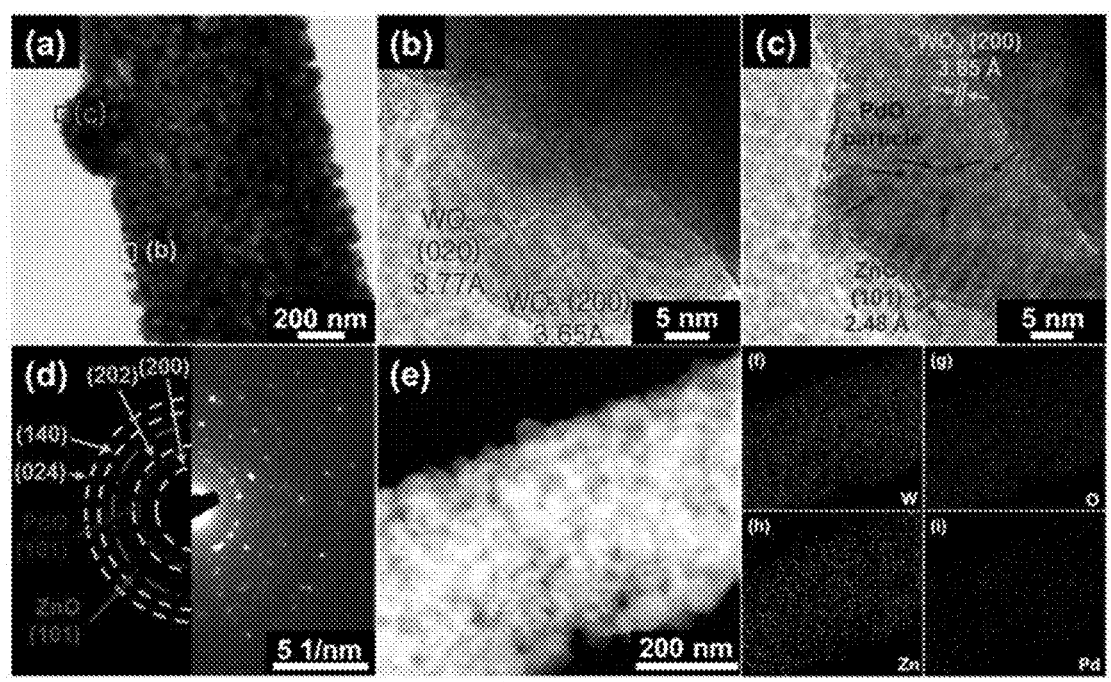
FIG. 8 is a TEM image and an energy dispersive X-ray spectrometer (EDS) image showing the porous semiconductor metal oxide complex nanofiber functionalized by uniformly distributing the porous ZnO particles including the PdO nanoparticle catalysts in the inside and on the surface of the $WO_3$ nanofiber, which is obtained after the thermal treatment according to the embodiment example 2 of the inventive concepts.

FIG. 8 is a TEM image showing the $WO_3$ complex nanofiber to which ZnO including the PdO nanoparticle catalyst is coupled, which is manufactured in the embodiment example 2. ZnO to which the PdO nanoparticle catalyst is coupled exists in the $WO_3$ nanofiber in lattice analysis using a TEM, and the PdO nanoparticle catalyst and ZnO crystallized in the $WO_3$ nanofiber are shown through a selected area electron diffraction (SAED) pattern. In addition, Pd and Zn uniformly distributed in the $WO_3$ nanofiber can be observed through an energy-dispersive X-ray spectroscopy (EDS) image obtained by the TEM analysis. In other words, it is recognized that ZnO including the PdO nanoparticle catalyst is uniformly distributed in the $WO_3$ nanofiber.

Comparison Example 1: Manufacture of ZnO/$WO_3$ Complex Nanofiber Using Metal-Organic Framework ZIF-8 not Including Nanoparticle Catalyst A $WO_3$ nanofiber to which metal-organic frameworks not including a nanoparticle catalyst are coupled is manufactured as a comparison example compared to the embodiment example 2. 0.4 g of AMH corresponding to a tungsten oxide precursor is added into and dissolved in 3 g of DI water at room temperature. Next, 200 mg of a pure metal-organic framework ZIF-8 water solution manufactured in the embodiment example 1 is added into and mixed with the tungsten oxide precursor water solution. To smoothly perform an electrospinning process by increasing viscosity of the mixed solution, 0.5 g of a PVP polymer having a molecular weight of about 1,300,000 g/mol is added into the mixed solution, and the mixed solution including the PVP polymer is stirred at room temperature for 5 hours at 500 rpm to prepare an electrospinning solution. The prepared electrospinning solution is provided in a syringe, and the syringe is connected to a syringe pump to discharge the electrospinning solution at a discharging rate of 0.1 ml/min. 15 kV is applied between a needle (21 gauge) used in the electrospinning process and a collector collecting nanofibers to perform the electrospinning process. A SUS plate was used as the collector of the nanofibers, and a distance between the needle and the collector was 15 cm.

A pure metal-organic framework/tungsten oxide precursor/polymer complex nanofiber manufactured by the above mentioned method was heated to 500□ at a heating rate of 4□/min and was then maintained at 500□ for 1 hour. Subsequently, the complex nanofiber was cooled to room temperature at a cooling rate of 40□/min. During the high-temperature thermal treatment, organic ligands of the metal-organic frameworks and the polymer are decomposed and removed and the metal ion ($Zn^{2+}$) of the metal-organic framework and the tungsten oxide precursor are oxidized to form ZnO and $WO_3$, respectively. Thus, a $WO_3$ nanofiber to which ZnO is coupled is formed.

Figure 9:
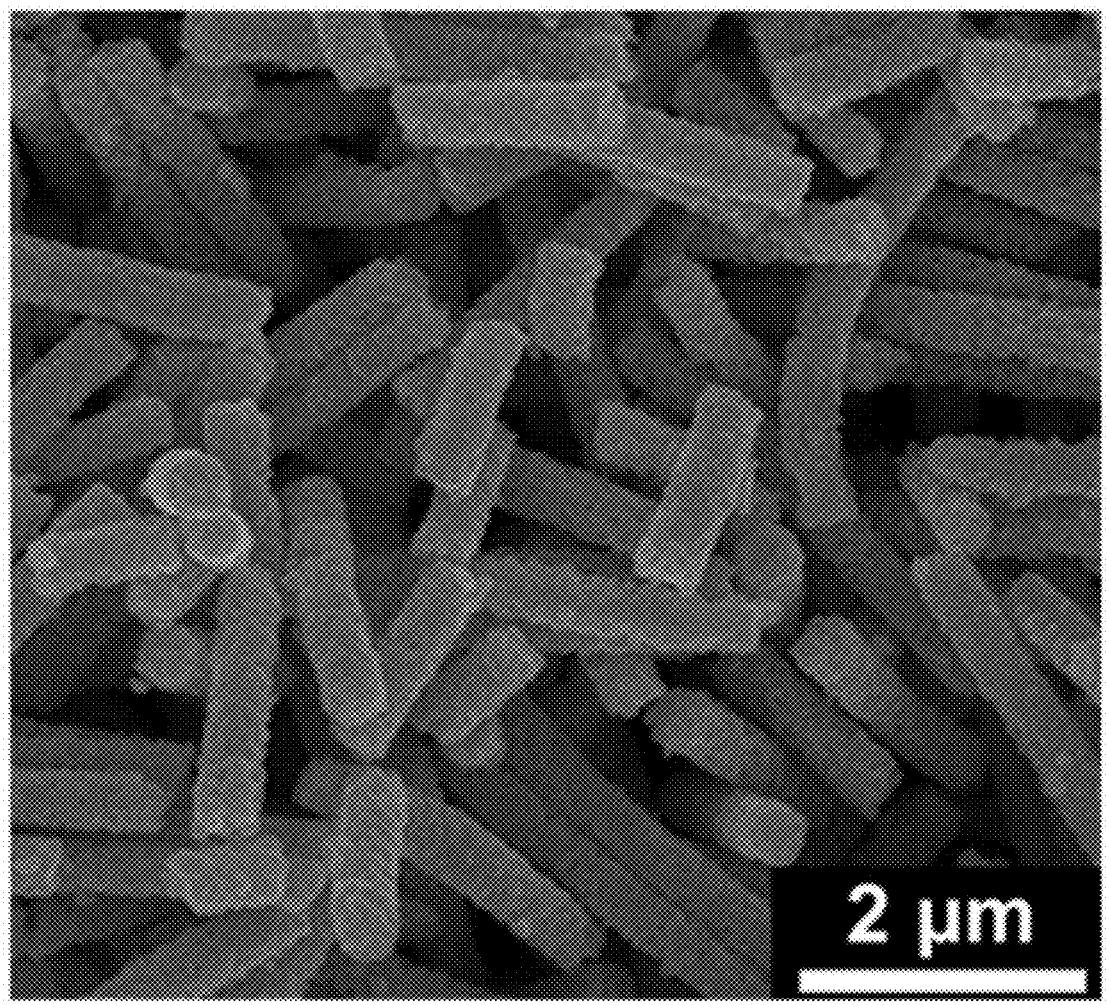
FIG. 9 is a SEM image showing a porous semiconductor metal oxide complex nanofiber functionalized by uniformly distributing porous ZnO particles, to which pure metal-organic frameworks manufactured according to a comparison example 1 are coupled, in an inside and on a surface of a $WO_3$ nanofiber.

FIG. 9 is a SEM image showing a ZnO/$WO_3$ complex nanofiber manufactured using the pure metal-organic frameworks in the comparison example 1. It is recognized that the manufactured ZnO/$WO_3$ complex nanofiber has a diameter of 400 nm to 600 nm.

The manufactured ZnO/$WO_3$ complex nanofiber not including a nanoparticle catalyst was used to compare sensing characteristics with respect to various gases along with the $WO_3$ nanofiber to which ZnO embedded with the PdO nanoparticle catalysts is coupled, which is manufactured in the embodiment example 2.

Comparison Example 2: Manufacture of Pure $WO_3$ Nanofiber not Including Metal-Organic Framework ZIF-8 and Nanoparticle Catalyst A pure $WO_3$ nanofiber not including a nanoparticle catalyst and a metal-organic framework is manufactured as another comparison example compared to the embodiment example 2. In detail, 0.5 g of PVP having a weight-average molecular weight of about 1,300,000 g/mol and 0.4 g of AMH being the tungsten oxide precursor are provided into 3 g of DI water, and the water solution including the PVP and the AMH is stirred at room temperature for 5 hours at 500 rpm. The tungsten oxide precursor/polymer complex electrospinning solution is a syringe for an electrospinning process after the stirring process, and then, the syringe is connected to a syringe pump to discharge the electrospinning solution at a discharging rate of 0.1 ml/min. A needle used in the electrospinning process is a 21 gauge needle. During the electrospinning process, a distance between the needle and a collector receiving nanofibers is about 15 cm and 15 kV is applied between the needle and the collector, thereby manufacturing a tungsten oxide precursor/polymer complex nanofiber web. A high-temperature thermal treatment process is performed on the manufactured tungsten oxide precursor/polymer complex nanofiber to remove the polymer and to oxidize the tungsten oxide precursor. At this time, the tungsten oxide precursor is oxidized to form $WO_3$. The high-temperature thermal treatment process is performed for one hour at 500□. At this time, a heating rate of 4□/min is maintained and a cooling rate of 40□/min is maintained.

Figure 10:
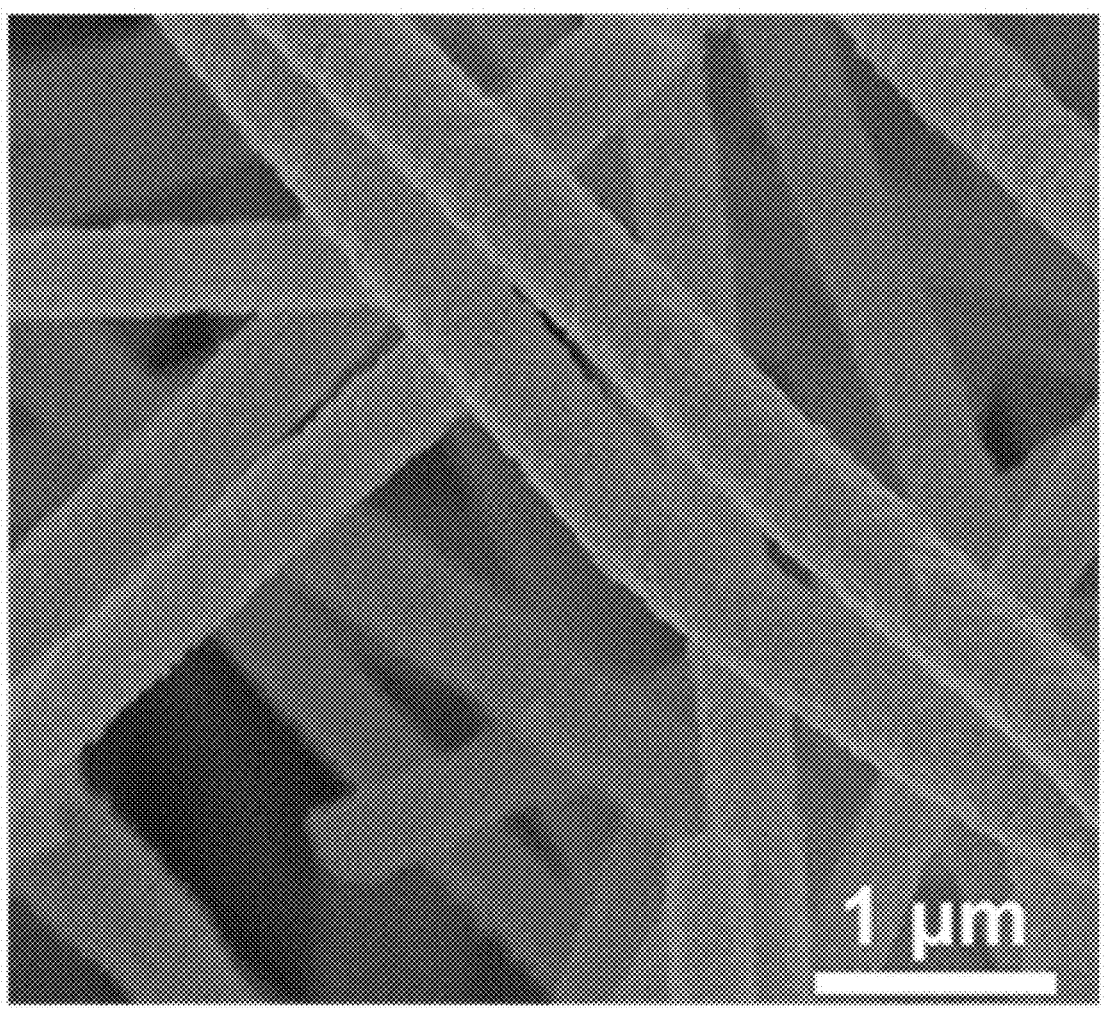
FIG. 10 is a SEM image showing a pure $WO_3$ nanofiber not including a nanoparticle catalyst and a metal-organic framework, which is manufactured according to a comparison example 2.

FIG. 10 is a SEM image showing the pure $WO_3$ nanofiber not including the nanoparticle catalyst and the metal-organic framework, which is manufactured in the comparison example 2. It is recognized that the manufactured $WO_3$ nanofiber has a diameter of about 400 nm to about 600 nm.

The manufactured pure $WO_3$ nanofiber was used to compare sensing characteristics with respect to various gases along with the $WO_3$ nanofiber to which ZnO uniformly embedded with the PdO nanoparticle catalysts is coupled, which is manufactured in the embodiment example 2.

Experimental Example 1: Manufacture and Characteristic Evaluation of Gas Sensor Using $WO_3$ Nanofiber to which ZnO Uniformly Embedded with PdO Nanoparticle Catalysts is Coupled, Gas Sensor Using $WO_3$ Nanofiber to which ZnO is Coupled, and Gas Sensor Using Pure $WO_3$ Nanofiber To manufacture exhaled breath sensors using the members manufactured in the embodiment examples 1 and 2 and the comparison examples 1 and 2, 5 mg of the $WO_3$ nanofiber to which ZnO uniformly embedded with PdO nanoparticle catalysts is coupled, 5 mg of the $WO_3$ nanofiber to which ZnO is coupled, and 5 mg of the pure $WO_3$ nanofiber were dispersed in 100 µl of ethanol solvents, respectively, and then, a pulverization process was performed on each of the solvents including these nanofibers by using ultrasonic cleaning. During the pulverization process, the synthesized nanofiber may be formed into a nanorod. A length of the nanorod is shorter than that of the synthesized nanofiber.

A top surface of an alumina substrate (3 mm×3 mm) on which two parallel gold electrodes spaced apart from each other by 300 µm were formed was coated with each of the $WO_3$ nanofiber to which ZnO uniformly embedded with PdO nanoparticle catalysts is coupled, the $WO_3$ nanofiber to which ZnO is coupled, and the pure $WO_3$ nanofiber by using a drop coating process. In the coating process, a portion of the alumina substrate, on which a sensor electrode exists, was coated with 2 µl of each of the $WO_3$ nanofiber to which ZnO uniformly embedded with PdO nanoparticle catalysts is coupled, the $WO_3$ nanofiber to which ZnO is coupled, and the pure $WO_3$ nanofiber dispersed in the ethanol by a micro-pipette, and then the alumina substrate was dried on a hot plate of 60□. These processes were repeated four, five or six times to sufficiently coat the alumina substrate with each of the $WO_3$ nanofiber to which ZnO uniformly embedded with PdO nanoparticle catalysts is coupled, the $WO_3$ nanofiber to which ZnO is coupled, and the pure $WO_3$ nanofiber.

In addition, response characteristics of exhaled breath sensors, manufactured above, with respect to an acetone ($CH_3COCH_3$) gas, a sulfureted hydrogen ($H_2S$) gas, and a toluene ($C_6H_5CH_3$) gas were evaluated at a driving temperature of 350 in a relative humidity (90% RH) similar to a humidity of a gas exhaled from a man's mouth while changing a gas concentration in an order of 5 ppm, 4 ppm, 3 ppm, 2 ppm, and 1 ppm. The acetone ($CH_3COCH_3$) gas, the sulfureted hydrogen ($H_2S$) gas, and the toluene ($C_6H_5CH_3$) gas correspond to biomarker gases for diabetes diagnosis, foul breath diagnosis, and lung cancer diagnosis, respectively. Furthermore, sensing characteristics of the exhaled breath sensors were evaluated with respect to a nitrogen monoxide (NO) gas, an ammonia ($NH_3$) gas, and ethanol ($C_2H_5OH$) as well as the acetone ($CH_3COCH_3$) gas, the sulfureted hydrogen ($H_2S$) gas, and the toluene ($C_6H_5CH_3$) gas, thereby evaluating selective gas sensing characteristics. The nitrogen monoxide (NO) gas and the ammonia ($NH_3$) gas correspond to biomarkers of asthma and kidney disease, respectively.

Figure 11:
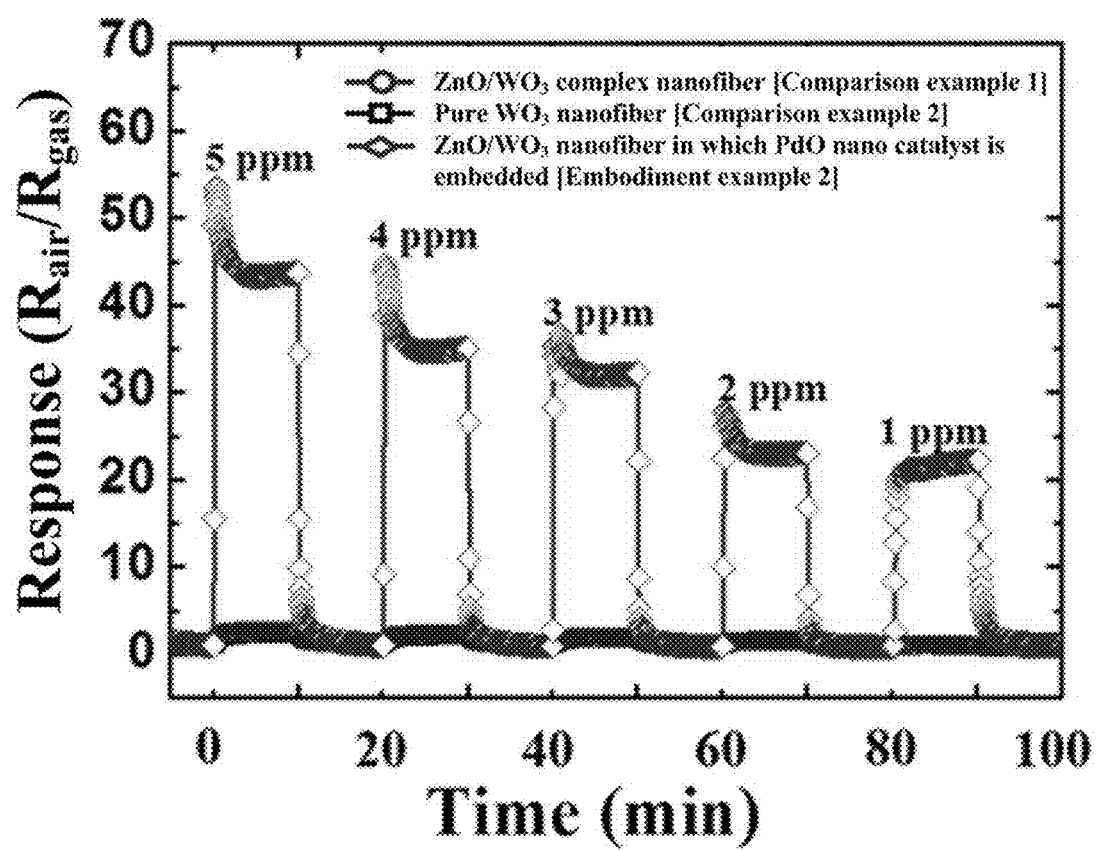
FIG. 11 is a graph showing responses, with respect to toluene gases (1 to 5 ppm) at 350□ of the porous semiconductor metal oxide complex nanofiber functionalized by uniformly distributing the porous ZnO particles including the PdO nanoparticle catalysts in the inside and on the surface of the $WO_3$ nanofiber according to the embodiment example 2, which is obtained in an experimental example 1 of the inventive concepts.

FIG. 11 is a graph showing response degrees ($R_{air}/R_{gas}$) according to time, which are obtained while reducing a concentration of the toluene gas in an order of 5 ppm, 4 ppm, 3 ppm, 2 ppm, and 1 ppm at 350□, where "$R_{air}$" denotes a resistance value of the metal oxide material when air is injected, and "$R_{gas}$" denotes a resistance value of the metal oxide material when the toluene gas is injected.

As shown in FIG. 11, the response characteristic to the toluene gas of the sensor using the $WO_3$ nanofiber 110 to which ZnO embedded uniformly embedded with the PdO nanoparticle catalysts is coupled is about 20 times higher than that of the sensor using the $WO_3$ nanofiber to which ZnO is coupled, and that of the sensor using the pure $WO_3$ nanofiber.

Figure 12:
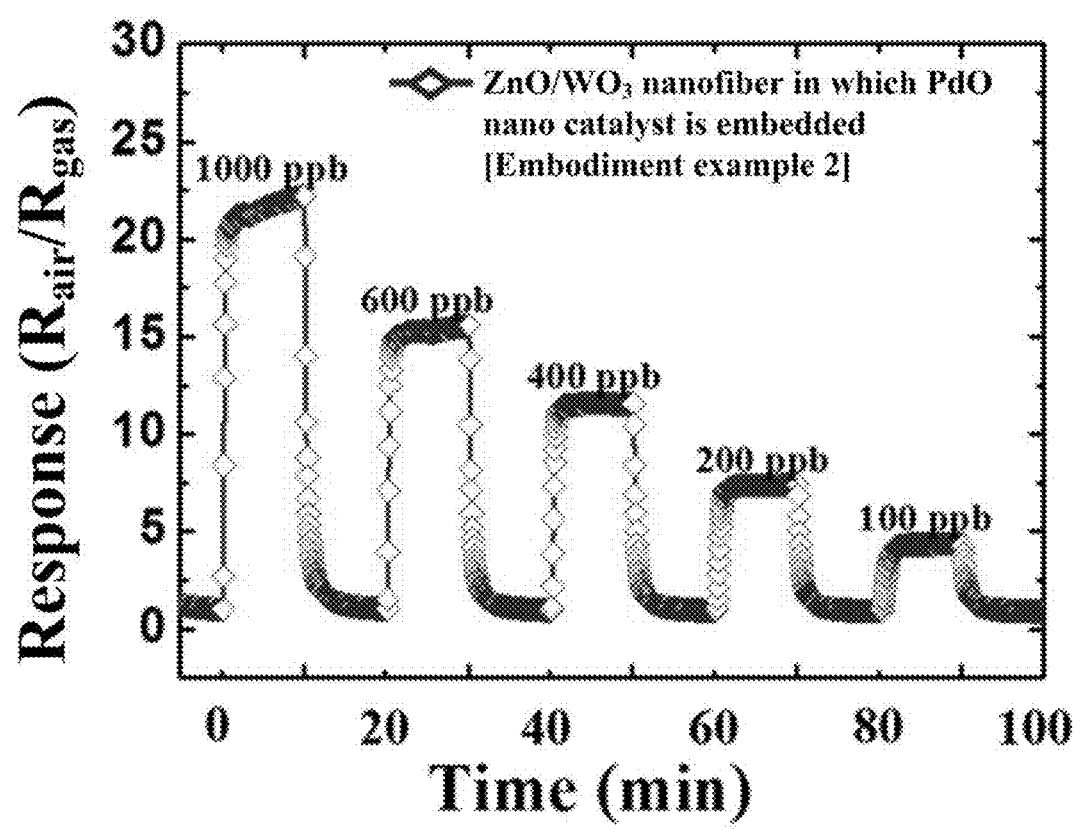
FIG. 12 is a graph showing responses, with respect to toluene gases (1, 0.6, 0.4, 0.2, and 0.1 ppm) at 350□, of the porous semiconductor metal oxide complex nanofiber functionalized by uniformly distributing the porous ZnO particles including the PdO nanoparticle catalysts in the inside and on the surface of the $WO_3$ nanofiber according to the embodiment example 2, which is obtained in the experimental example 1 of the inventive concepts.

FIG. 12 is a graph showing response degrees according to time, which are obtained while reducing a concentration of the toluene gas in an order of 1 ppm, 0.6 ppm, 0.4 ppm, 0.2 ppm, and 0.1 ppm at 350□. As shown in FIG. 12, the response characteristic to the toluene gas of the sensor using the $WO_3$ nanofiber 110 to which ZnO embedded uniformly embedded with the PdO nanoparticle catalysts is coupled has a high sensitivity of about 4.5 at 0.1 ppm.

Figure 13:
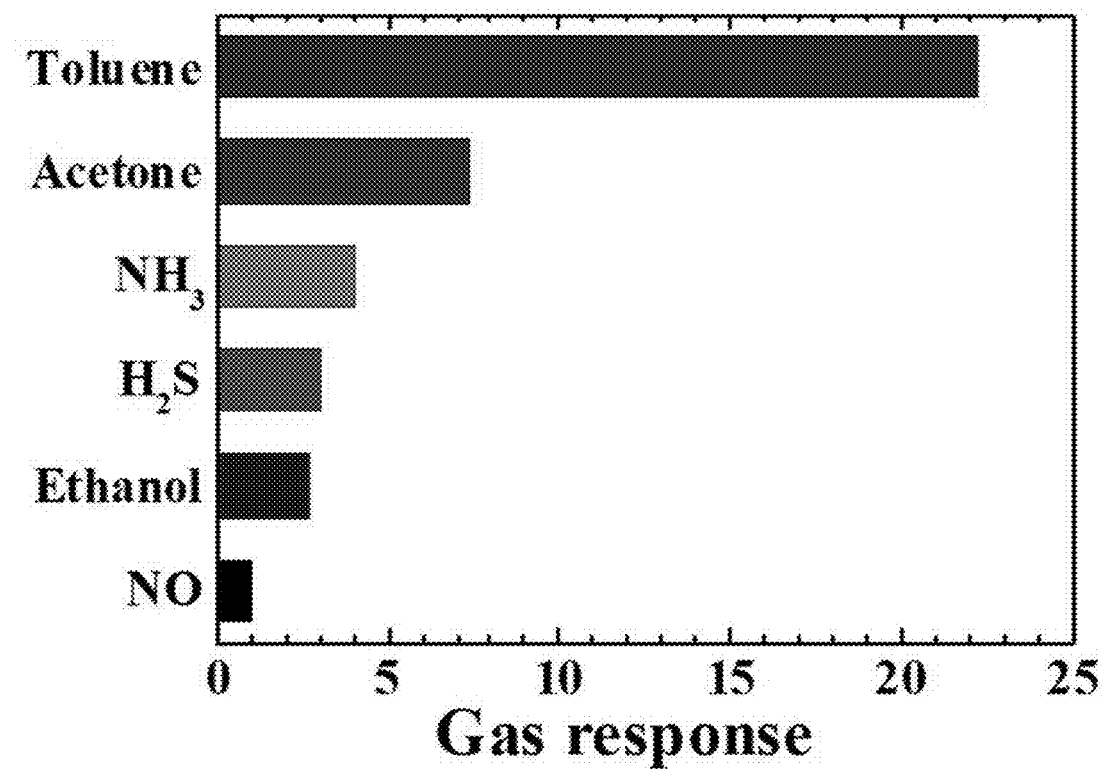
FIG. 13 is a graph showing responses, with respect to biomarker gases (i.e., toluene ($C_6H_5CH_3$), acetone ($CH_3COCH_3$), ammonia ($NH_3$), sulfureted hydrogen ($H_2S$), ethanol ($C_2H_5OH$), and nitrogen monoxide (NO)) at 350□ at 1 ppm, of the porous semiconductor metal oxide complex nanofiber functionalized by uniformly distributing the porous ZnO particles including the PdO nanoparticle catalysts in the inside and on the surface of the $WO_3$ nanofiber according to the embodiment example 2, which is obtained in the experimental example 1 of the inventive concepts.

FIG. 13 is a graph showing response degrees to the acetone gas, the ammonia gas, the sulfureted hydrogen gas, the ethanol gas, the nitrogen monoxide gas, and the toluene gas, which are obtained at 350□ at a concentration of 1 ppm by the sensor using the $WO_3$ nanofiber 110 to which ZnO embedded uniformly embedded with the PdO nanoparticle catalysts is coupled. The toluene gas is known as a biomarker gas of the lung cancer.

As shown in FIG. 13, the sensor using the $WO_3$ nanofiber 110 including ZnO embedded uniformly embedded with the PdO nanoparticle catalysts has an excellent selective sensing characteristic with respect to the toluene gas corresponding to the biomarker gas of the lung cancer, as compared to the acetone gas, the ammonia gas, the sulfureted hydrogen gas, the ethanol gas, and the nitrogen monoxide gas corresponding to the biomarker gases of other diseases.

The high sensitivity and high selectivity of the $WO_3$ nanofiber including ZnO uniformly embedded with the PdO nanoparticle catalysts with respect to the toluene gas are shown in the experimental example described above. In the sensor manufactured using the $WO_3$ nanofiber including the metal-organic frameworks embedded with the nanoparticle catalysts as a sensing material, the nanoparticle catalyst and the metal-organic framework may be changed to manufacture sensors having high sensitivity and high selectivity with respect to other gases. In addition, a kind of the metal oxide material may be changed to allow the sensor to have an additional selective variation characteristic, and thus a nano sensor array having high sensitivity and high selectivity may be manufactured using various kinds of first metal oxide/second metal oxide complex nanofibers to which various kinds of nanoparticle catalyst particles are coupled. The metal oxide/metal oxide complex nanofiber sensing material in which the nanoparticle catalysts obtained from the metal-organic framework template are embedded may be used in an excellent harmful environmental gas sensor and a healthcare gas sensor for analyzing and diagnosing a volatile organic compound gas included in the exhaled breath.

According to some embodiments of the inventive concepts, when the metal-organic frameworks including the nanoparticle catalysts are dispersed in the electrospinning solution to synthesize the porous semiconductor metal oxide complex nanofiber sensing material including the nanoparticle catalysts, the nanoparticle catalysts may provide the electronic or chemical sensitization effect, and the rust metal oxide particle and the second metal oxide nanofiber may form the heterojunction in an N-type/N-type, N-type/P-type or P-type/P-type form. Thus, the nanofiber sensor having excellent sensitivity and selectivity may be manufactured. In particular, since a metal (nanoparticle catalyst)/metal oxide (first metal oxide particle)/metal oxide (second metal oxide nanofiber) complex or a metal oxide (nanoparticle catalyst)/metal oxide (first metal oxide particle)/metal oxide (second metal oxide nanofiber) complex is formed in various combination, a library having excellent selectivity may be provided when a sensor array having various kinds is manufactured. In addition, the nanoparticle catalysts are inserted in the cavities of the unit metal-organic frameworks, and the metal-organic framework molecular sieves including the unit metal-organic frameworks are uniformly dispersed in the nanofiber. Since the catalyst particles are dispersed without aggregation, the catalyst effect may be excellent. Furthermore, the organic ligands of the metal-organic frameworks may be removed during the thermal treatment, and thus fine pores may be generated in the nanofiber. As a result, it is possible to provide the gas sensor member having the excellent gas response characteristics, the gas sensor using the same, and the method of manufacturing the same.

While the inventive concepts have been described with reference to example embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A compound, comprising porous metal oxide particles and nanoparticle catalysts embedded therein, said porous metal oxide particles substantially uniformly dispersed in an inside and on a surface of a metal oxide nanofiber, wherein said porous metal oxide particles substantially uniformly dispersed in said inside of said metal oxide nanofiber are enveloped by said metal oxide nanofiber.

2. The compound of claim 1, wherein the nanoparticle catalysts are in cavities of the metal oxide particles.

3. The compound of claim 2, wherein sizes of the cavities of the metal oxide particles range from 0.9 nm to 30 nm, and
wherein an outside diameter of the metal oxide nanofiber ranges from 20 nm to 2 μm.

4. The compound of claim 1, wherein a weight ratio of the nanoparticle catalysts ranges from 0.001 wt % to 25 wt % with respect to the metal oxide particles and ranges from 0.001 wt % to 0.5 wt % with respect to the metal oxide nanofiber.

5. The compound of claim 1, wherein the nanoparticle catalysts include at least one nanoparticle catalyst selected from a group consisting of Pt, Pd, Rh, Ru, Ni, Co, Cr, Ir, Au, Ag, Zn, W, Sn, Sr, In, Pb, Fe, Cu, V, Ta, Sb, Sc, Ti, Mn, Ga, and Ge.

6. The compound of claim 1, wherein the nanoparticle catalysts include at least one nanoparticle catalyst selected from a group consisting of Pt, PdO, $PdO_2$, $Rh_2O_3$, $RuO_2$, NiO, $Co_3O_4$, $Cr_2O_3$, $IrO_2$, Au, Ag, ZnO, $WO_3$, $SnO_2$, SrO, $In_2O_3$, PbO, $Fe_2O_3$, CuO, $V_2O_5$, $VO_2$, VO, $Ta_2O_5$, $Sb_2O_3$, $Sc_2O_3$, $TiO_2$, $MnO_2$, $Ga_2O_3$, and $GeO_2$.

7. The compound of claim 1, wherein an outer surface of the metal oxide nanofiber is formed of metal ions having electric charges.

8. The compound of claim 1, wherein the metal oxide particles include at least one metal oxide selected from a group consisting of ZnO, $Fe_2O_3$, $Fe_3O_4$, NiO, CuO, $In_2O_3$, $Co_3O_4$, $NiCo_2O_4$, $ZrO_2$, $Cr_3O_4$, $MnO_2$, and MgO.

9. The compound of claim 1, wherein the metal oxide particles have the shape of hollow spheres or hollow cubes.

10. The compound of claim 1, wherein the metal oxide nanofiber has a chemical composition selected from a group consisting of ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $ZrO_2$, $Al_2O_3$, $B_2O_3$, $V_2O_5$, $Cr_3O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $RuO_2$, $IrO_2$, $MnO_2$, $InTaO_4$, ITO, IZO, $InTaO_4$, MgO, $Ga_2O_3$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, and $Ba_{0.5}Sr_{0.8}Co_{0.8}Fe_{0.2}O_{3-7}$.

11. The compound of claim 1, wherein the metal oxide particles and the metal oxide nanofiber combine to form heterojunctions,
wherein the heterojunctions are an N-type metal oxide/N-type metal oxide combination, an N-type metal oxide/P-type metal oxide combination, or a P-type metal oxide/P-type metal oxide combination.

12. The compound of claim 11, wherein the heterojunctions are an N-type metal oxide/N-type metal oxide combination, and wherein the N-type metal oxides include at least one selected from a group consisting of $TiO_2$, ZnO, $WO_3$, $SnO_2$, $IrO_2$, $In_2O_3$, $V_2O_3$, and $MoO_3$.

13. The compound of claim 11, wherein the heterojunctions are a P-type metal oxide/P-type metal oxide combination, and wherein the P-type metal oxides include at least one selected from a group consisting of $Ag_2O$, $PdO$, $RuO_2$, $Rh_2O_3$, $NiO$, $Co_3O_4$, $CuO$, $Fe_2O_3$, $Fe_3O_4$, $V_2O_5$, and $Cr_2O_3$.

14. The compound of claim 11, wherein the heterojunctions are an N-type metal oxide/P-type metal oxide combination, wherein the N-type metal oxides include at least one selected from a group consisting of $TiO_2$, $ZnO$, $WO_3$, $SnO_2$, $IrO_2$, $In_2O_3$, $V_2O_3$, and $MoO_3$, and wherein the P-type metal oxides include at least one selected from a group consisting of $Ag_2O$, $PdO$, $RuO_2$, $Rh_2O_3$, $NiO$, $Co_3O_4$, $CuO$, $Fe_2O_3$, $Fe_3O_4$, $V_2O_5$, and $Cr_2O_3$.

15. A gas sensor comprising the compound of claim 1 on a sensor substrate.

16. The compound of claim 1, wherein the nanoparticle catalysts are metal oxide nanoparticle catalysts.

17. The compound of claim 1, wherein the metal oxide particles comprises cavities with sizes from 0.9 nm to 30 nm in which the nanoparticle catalysts are embedded.

18. The compound of claim 1, wherein the metal oxide particles are substantially uniformly dispersed in said inside and on said surface of said metal oxide nanofiber without aggregation.

19. The compound of claim 1, wherein the nanoparticle catalysts are in inner cavities of the metal oxide particles.

20. The compound of claim 1, wherein the nanoparticle catalysts are uniformly embedded in the metal oxide particles.

\* \* \* \* \*